United States Patent
Keller

(10) Patent No.: US 10,863,974 B2
(45) Date of Patent: Dec. 15, 2020

(54) TISSUE STRIP CONTAINER FOR FORMALIN FIXATION

(71) Applicant: Devicor Medical Products, Inc., Cincinnati, OH (US)

(72) Inventor: Bryan R. Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 206 days.

(21) Appl. No.: 15/729,262

(22) Filed: Oct. 10, 2017

(65) Prior Publication Data

US 2018/0098755 A1    Apr. 12, 2018

Related U.S. Application Data

(60) Provisional application No. 62/406,473, filed on Oct. 11, 2016.

(51) Int. Cl.
*A61B 10/02* (2006.01)
*A61B 10/00* (2006.01)

(52) U.S. Cl.
CPC ...... *A61B 10/0096* (2013.01); *A61B 10/0275* (2013.01); *A61B 10/0283* (2013.01); *A61B 2010/0225* (2013.01)

(58) Field of Classification Search
None
See application file for complete search history.

(56) References Cited

U.S. PATENT DOCUMENTS

| 5,526,822 | A  | 6/1996  | Burbank et al.  |
| 5,928,164 | A  | 7/1999  | Burbank et al.  |
| 6,017,316 | A  | 1/2000  | Ritchart et al. |
| 6,086,544 | A  | 7/2000  | Hibner et al.   |
| 6,162,187 | A  | 12/2000 | Buzzard et al.  |
| 6,432,065 | B1 | 8/2002  | Burdorff et al. |

(Continued)

FOREIGN PATENT DOCUMENTS

| WO | WO 2013/192606 A1 | 12/2013 |
| WO | WO 2013/192607 A1 | 12/2013 |

(Continued)

OTHER PUBLICATIONS

Hahn, M., et al., "Diagnostic Primer: Vacuum-Assisted Breast Biopsy with Mammotome®," Devicor Medical Germany GmBh, Nov. 11, 2012, Germany, Springer Medizin Verlag, copyright 2013, 130 pgs.

(Continued)

*Primary Examiner* — Marjan Fardanesh
(74) *Attorney, Agent, or Firm* — Frost Brown Todd LLC

(57) ABSTRACT

A tissue acquisition and handling system includes a biopsy device, a tray, and a container. The biopsy device includes a needle and a tissue sample holder assembly. The needle is configured to acquire tissue samples and communicate tissue samples to the tissue sample holder assembly. The tray includes a plurality of strips. The tray is configured to be receiving within the tissue sample holder assembly of the biopsy device. The container includes a plurality of tray receiving portions. Each tray receiving portion includes a distal end, a proximal end, and a tray chamber, the tray chamber extends between the proximal end and the distal end. The tray chamber is configured to receive at least a portion of the tray through a tray opening of the proximal end.

4 Claims, 17 Drawing Sheets

(56) References Cited

U.S. PATENT DOCUMENTS

| | | | |
|---|---|---|---|
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,648,466 B2 | 1/2010 | Stephens et al. | |
| 7,715,523 B2 | 5/2010 | Lafferty | |
| 7,837,632 B2 | 11/2010 | Stephens et al. | |
| 7,854,706 B2 | 12/2010 | Hibner | |
| 7,854,707 B2 * | 12/2010 | Hibner | A61B 10/0041 600/567 |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,251,916 B2 | 8/2012 | Speeg et al. | |
| 8,454,531 B2 | 6/2013 | Speeg et al. | |
| 8,503,602 B2 | 8/2013 | Lafferty | |
| 8,532,747 B2 | 9/2013 | Nock et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,802,034 B2 | 8/2014 | Bartfeld et al. | |
| 8,858,465 B2 | 10/2014 | Fiebig | |
| 8,938,285 B2 | 1/2015 | Fiebig et al. | |
| 9,056,317 B2 | 6/2015 | Bartfeld et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,409,164 B2 | 8/2016 | Tawfik et al. | |
| 9,486,186 B2 | 11/2016 | Fiebig et al. | |
| 9,877,706 B2 | 1/2018 | Speeg et al. | |
| 9,955,955 B2 | 5/2018 | Fiebig et al. | |
| 2006/0074345 A1 | 4/2006 | Hibner | |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2013/0324882 A1 | 12/2013 | Mescher | |
| 2014/0039343 A1 | 2/2014 | Mescher et al. | |
| 2015/0209017 A1 | 7/2015 | Fleming et al. | |
| 2016/0183928 A1 | 6/2016 | Speeg et al. | |
| 2018/0000463 A1 | 1/2018 | Keller | |

FOREIGN PATENT DOCUMENTS

| | | |
|---|---|---|
| WO | WO 2014/151603 A1 | 9/2014 |
| WO | WO 2015/042107 A1 | 3/2015 |

OTHER PUBLICATIONS

Lecia Microsystems, "Total Histology Solutions: Lecia Microsystems' Complete Histology Product Range," Sep. 2010, 28 pgs.

Rolls, G., "101 Steps to Better Histology," Lecia Biosystems, 2016, Lecia Biosystems Melbourne Pty. Ltd., Melbourne, Australia, 140 pgs.

Rolls, G., "An Introduction to Tissue Processing," Lecia Biosystems, 2016, Lecia Biosystems Melbourne Pty. Ltd., Melbourne, Australia, 57 pgs.

International Search Report and Written Opinion dated Mar. 21, 2018 for Application No. PCT/US2017/055904, 16 pgs.

U.S. Appl. No. 62/406,473, filed Oct. 11, 2016.

* cited by examiner

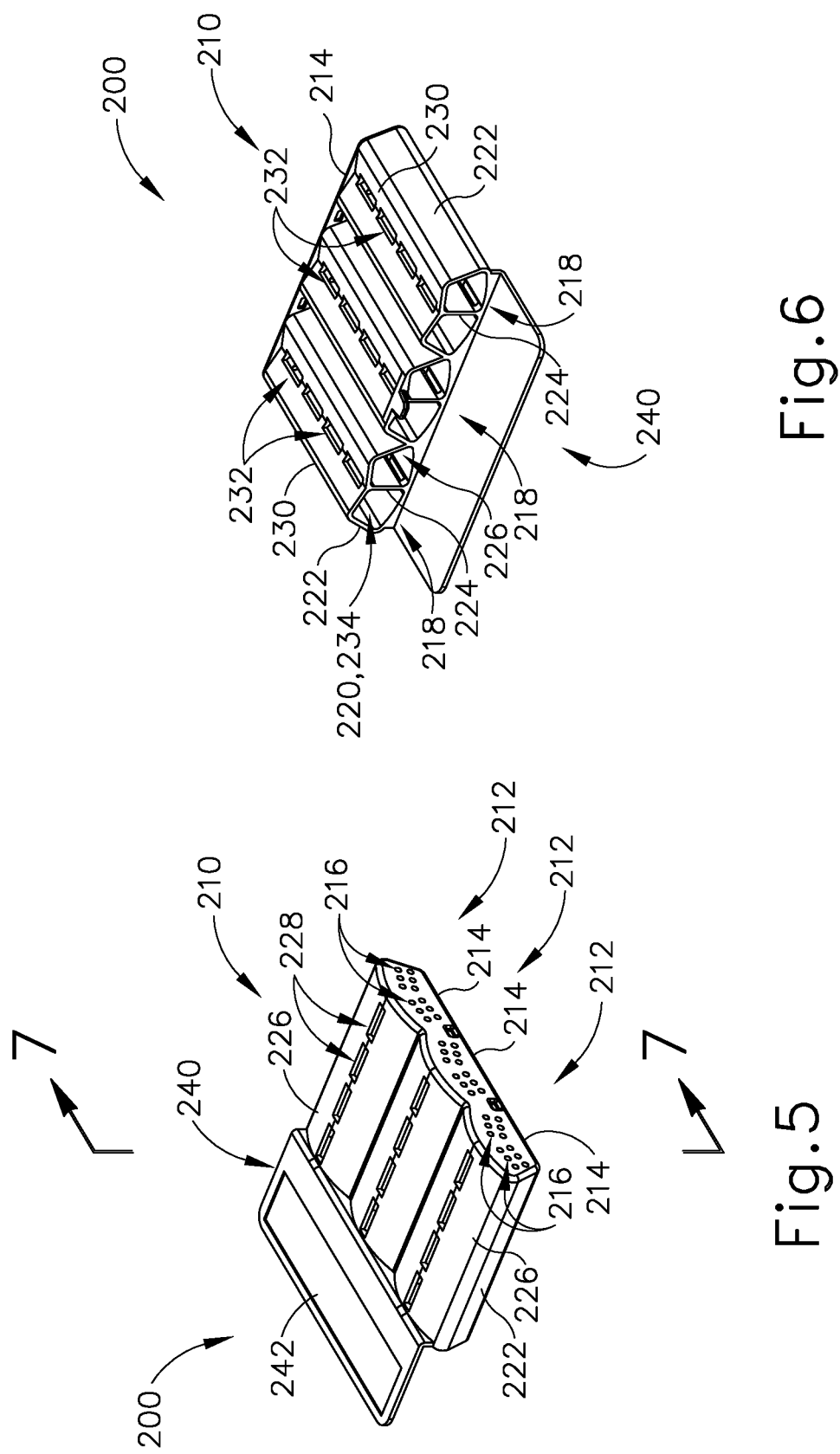

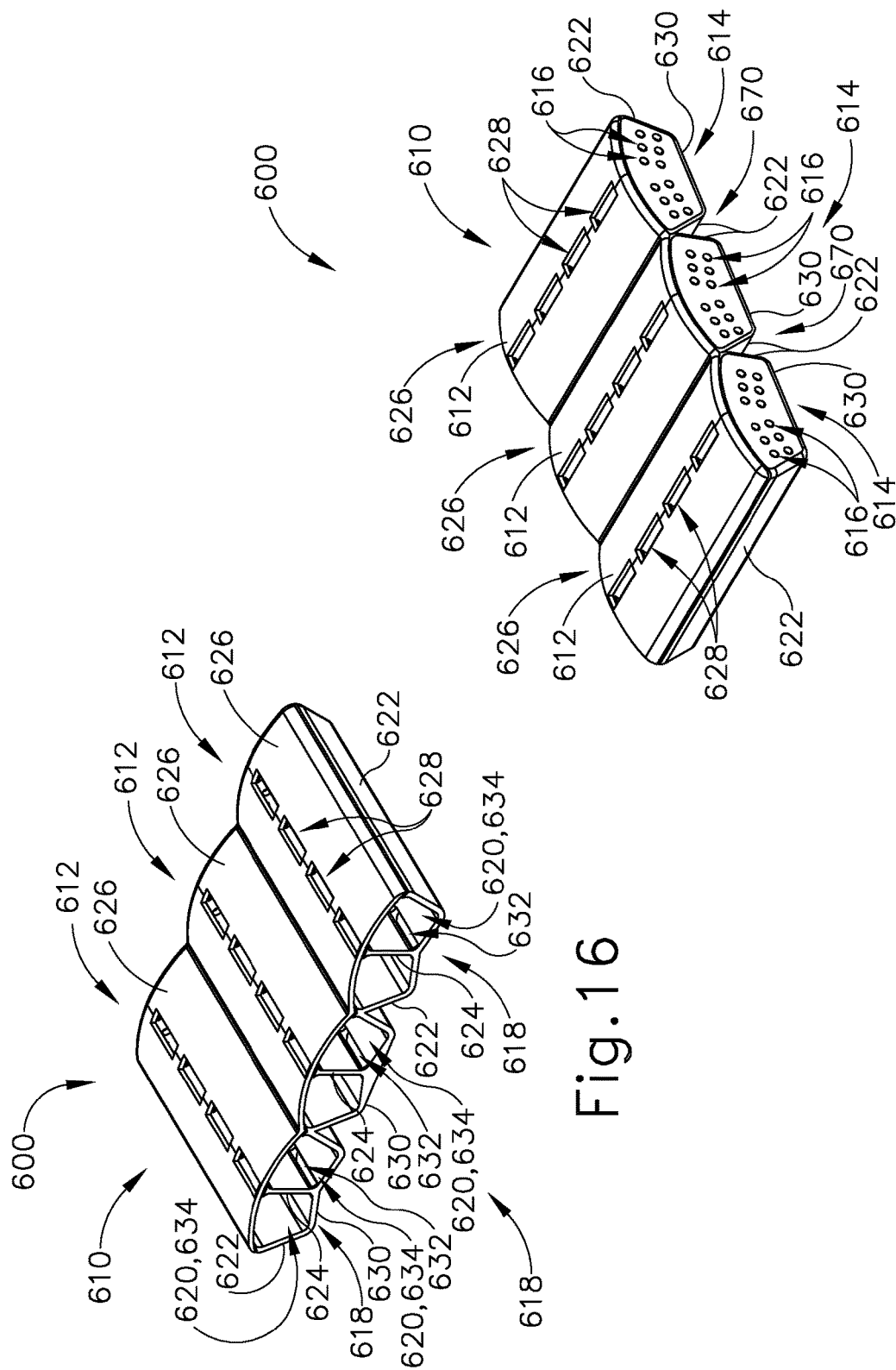

TISSUE STRIP CONTAINER FOR FORMALIN FIXATION

PRIORITY

The present application claims priority to U.S. Provisional Patent Application No. 62/406,473, entitled "TISSUE STRIP CONTAINER FOR FORMALIN FIXATION," filed on Oct. 11, 2016, the disclosure of which is hereby incorporated by reference herein in its entirety.

BACKGROUND

A biopsy is the removal of a tissue sample to examine tissue for signs of cancer or other disorders. Tissue samples are obtained in a variety of ways using various medical procedures involving a variety of the sample collection devices. For example, biopsies may be open (surgically removing tissue) or percutaneous (e.g. by fine needle aspiration, core needle biopsy or vacuum assisted biopsy). After the tissue sample is collected, the tissue sample is analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

The state of the art for breast biopsy is vacuum-assisted breast biopsy. A current textbook in this area is "Vacuum-Assisted Breast Biopsy with Mammotome", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator will create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using medically acceptable ways to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure will proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using medically acceptable ways to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015; U.S. Pat. No. 9,326,755, entitled "Biopsy Device Tissue Sample Holder with Bulk Chamber and Pathology Chamber," issued May 3, 2016; and U.S. Pat. No. 9,345,457, entitled "Presentation of Biopsy Sample by Biopsy Device," issued May 24, 2016. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006 and now abandoned; U.S. Pat. Pub. No. 2009/0131821, entitled "Graphical User Interface For Biopsy System Control Module," published May 21, 2009, now abandoned; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0144188, entitled "Biopsy Device With Slide-In Probe," published Jun. 6, 2013; and U.S. Pat. Pub. No. 2013/0324882, entitled "Control for Biopsy Device," published Dec. 5, 2013, now abandoned. The disclosure of each of the above-cited U.S. Non-Provisional patent applications is incorporated by reference herein.

U.S. Pub. No. 2014/0275999, entitled "Biopsy device" published on 18 Sep. 2014. U.S. Pub. No. 2016/0183928, entitled "Biopsy Device" published on 30 Jun. 2016. Both of these published patent applications describe and claim some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and a arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

Leica Biosystems is a global leader in workflow solutions and automation, providing anatomic pathology labs and researchers a comprehensive product range for each step in the pathology process from sample preparation and staining to imaging and reporting. Leica Biosystems has published on their website informational booklets that are accessible via download and that contain information on various aspects of the pathology process. These booklets include, but are not limited to: "An Introduction to Tissue Processing" by Geoffrey Rolls, "101 Steps to Better Histology," and "Total Histology Solutions," all of which are available via www.leicabiosystems.com.

At several steps during tissue processing using conventional techniques and instruments, it may be necessary to manually manipulate the tissue. This manual manipulation takes time and introduces the possibility of human error causing mistakes during the processing of tissue. Any and all mistakes during the processing of tissue will make the pathological examination of the tissue much more problematic to achieve the desired goal of having an accurate diagnosis. Thus, it is understood that a desired goal of modern tissue processing is the reduction of the requirement that tissue be manually manipulated.

International Pat. Pub. No. WO 2013/192606, entitled "Biopsy Tissue Sample Transport Device and Method of Using Thereof," published on Dec. 27, 2013 describes a biopsy tissue sample transport device and method of using thereof including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue storage assembly; and a lid to engage and substantially seal the assembly insertion opening of the housing.

International Pat. Pub. No. WO 2013/192607, entitled "Tissue Sample Container and Methods," published on Dec. 27, 2013, describes a tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

International Pat. Pub. No. WO 2014/151603, entitled "Biopsy Device," published on Sep. 25, 2014, describes a biopsy device includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

U.S. Pat. No. 7,715,523, entitled "System and Apparatus for Rapid Stereotactic Breast Biopsy Analysis," issued on May 11, 2010, and U.S. Pat. No. 8,503,602, entitled "System and Apparatus for Rapid Stereotactic Breast Biopsy Analysis," issued on Aug. 6, 2013, both describe a stereotactic breast biopsy apparatus and system that may comprise an x-ray source, a digital imaging receptor, and a biopsy specimen cassette, wherein the x-ray source is provided with a means for displacing the beam axis of the x-ray source from a working biopsy corridor beam axis to permit an unobstructed illumination of the biopsy specimen and thereby produce biopsy x-ray images directly in the procedure room for immediate analysis. Some examples of the benefits may be, but are not limited to, a more rapid analysis of biopsy specimen digital images, post-processing image capability, and decreased procedure time and diminution of patient bleeding complications and needle discomfort.

U.S. Pat. No. 8,485,987, entitled "Tissue Handling System with Reduced Operator Exposure," issued Jul. 16, 2016, describes a tissue handling system includes a biopsy device having an invasive unit with tissue-receiving and tissue-severing components being capable of harvesting and bringing at least one tissue sample to a point outside the body of a patient. The tissue handling system further includes a tissue collecting device adapted to be brought in detachable operative engagement with the tissue-receiving components of the biopsy device to remove the at least one tissue sample. Additionally, the tissue handling device comprises a tissue storage container configured to receive the at least one tissue sample, the entire tissue collecting device, or the part of the collecting device that contains the at least one tissue sample. The tissue storage container further is configured to receive a volume of preserving agent. The tissue handling system also comprises a vessel including the preserving agent adapted to be gas-tightly mated or coupled to the tissue storage container.

U.S. Pat. No. 8,802,034, "Tissue Container for Molecular and Histology Diagnostics Incorporating a Breakable Membrane," issued on Aug. 12, 2014, describes a container for storing a biological sample for molecular diagnostic testing and/or histological testing. The container includes a first chamber for receiving a sample holder therein, a second chamber, and a closure for enclosing the container. A breakable membrane, such as a pierce-able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

U.S. Pat. No. 9,056,317, "Tissue Container for Molecular and Histology Diagnostics Incorporating a Breakable Membrane," issued on Jun. 16, 2016. Describes a container for storing a biological sample for molecular diagnostic testing and/or histological testing. The container includes a first chamber for receiving a sample holder therein, a second chamber, and a closure for enclosing the container. A breakable membrane, such as a pierce able foil, extends within the container and separates the two chambers. When the breakable membrane is broken, fluid can pass between the first and second chambers. The membrane may be broken through an activator on the closure, such as a depressible member or a rotatable carrier, causing the sample holder to break through the membrane.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 5 depicts a perspective view of an exemplary container for use with the tray of FIG. 3;

FIG. 6 depicts another perspective view of the container of FIG. 5;

FIG. 16 depicts a perspective view of yet another exemplary alternative container for use with the tray of FIG. 3;

FIG. 17 depicts another perspective view of the container of FIG. 16;

Figure 1:
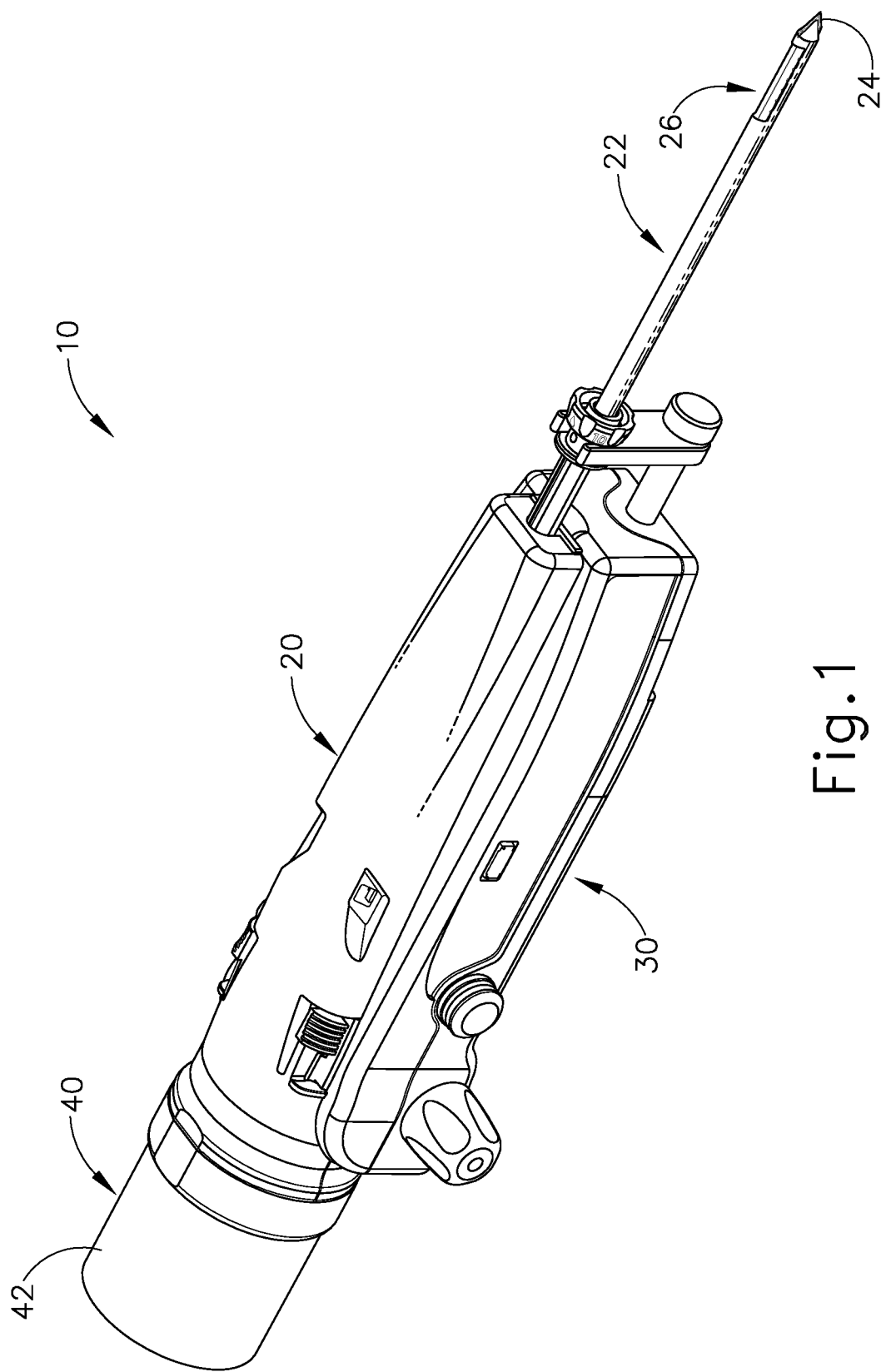
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Biopsy Device

FIG. 1 depicts an exemplary biopsy device (10) that can be used to acquire tissue samples from a patient. Biopsy device (10) comprises a probe assembly (20), a holster assembly (30), and a tissue sample holder assembly (40). Probe assembly (20) includes a distally projecting needle (22) that has a tissue piercing tip (24) and a lateral aperture (26) that is located proximal to tip (24). A tubular cutter (not shown) is slidably disposed in needle (22) and is operable to sever tissue that is protruding through lateral aperture (26). The severed tissue samples are communicated proximally through the lumen of the cutter to tissue sample holder assembly (40), as described below. In some versions, probe assembly (20) is coupled with a control module that is operable to provide communication of vacuum, saline, and/or atmospheric air to probe assembly (20).

Holster assembly (30) includes features that are operable to drive the cutter, features that are operable to fire needle (22) distally into tissue, and features that are operable to rotate needle (22) about a longitudinal axis of needle (22). In some versions, holster assembly (30) is coupled with a control module via a cable that is operable to provide electrical power and/or other electrical signals to holster assembly (30). In addition, or in the alternative, holster assembly (30) may receive a pressurized medium (e.g., air, hydraulic fluid, etc.) in order to provide motive force to drive the cutter of probe assembly (20).

In the present example, probe assembly (20) and holster assembly (30) are configured for use in a stereotactic image guided biopsy procedure. By way of example only, probe assembly (20) and holster assembly (30) may be constructed and operable in accordance with at least some of the teachings of U.S. Pub. No. 2014/0039343, entitled "Biopsy System," published Feb. 6, 2014, the disclosure of which is incorporated by reference herein. Alternatively, probe assembly (20) and holster assembly (30) may be configured for use in (or otherwise be used in) an ultrasound image guided biopsy procedure and/or an MRI guided biopsy procedure. By way of further example only, probe assembly (20) and holster assembly (30) may be constructed and operable in accordance with at least some of the teachings of U.S. Pub. No. 2013/0150751, entitled "Biopsy Device with Slide-In Probe," published Jun. 13, 2013, the disclosure of which is incorporated by reference herein. Alternatively, probe assembly (20) and holster assembly (30) may be constructed and operable in any other suitable fashion.

Figure 2:
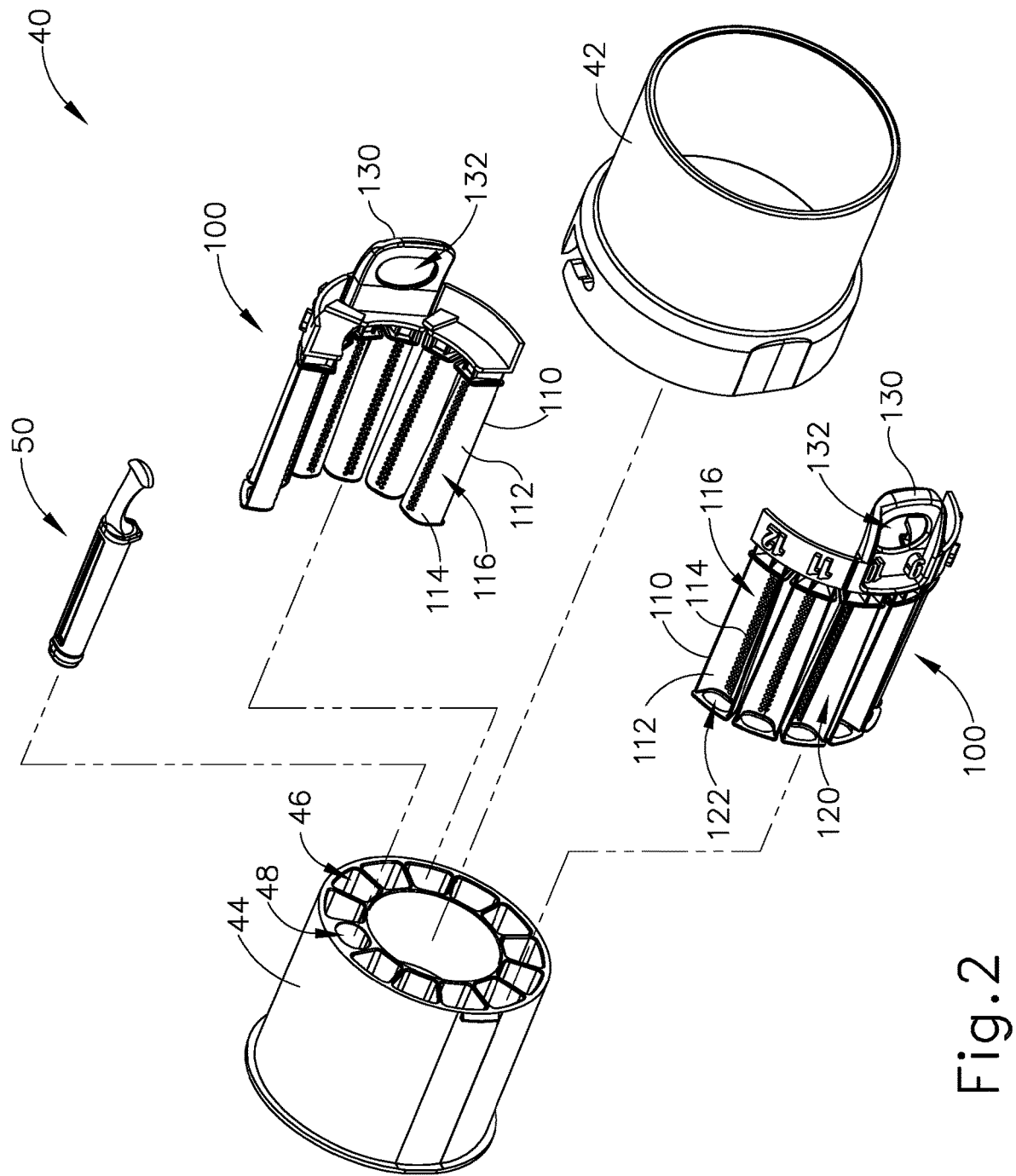
FIG. 2 depicts an exploded perspective view of a tissue sample holder assembly of the biopsy device of FIG. 1.

As noted above, tissue sample holder assembly (40) is configured to receive tissue samples that are severed by the cutter from tissue protruding through lateral aperture (26). As shown in FIG. 2, tissue sample holder assembly (40) of this example comprises a cylindraceous outer cover (42) that is removably coupled with probe assembly (20). A rotatable

(44) member is rotatably positioned within cover (42). Rotatable member (44) defines an angularly spaced array of strip receiving chambers (46) and a plug chamber (48), such that chambers (46, 48) together an annular arrangement. Rotatable member (44) is rotatable relative to probe assembly (20) to selectively index chambers (46, 48) relative to the cutter. In some versions, drive components in holster assembly (30) drive rotation of rotatable member (44). In some other versions, rotatable member (44) is driven manually by the operator manually grasping some portion of tissue sample holder assembly (40).

As also shown in FIG. 2, tissue sample holder assembly (40) further includes a pair of tissue sample trays (100). Each tissue sample tray (100) comprises a set of distally projecting tissue sample strips (110). Each tissue sample strip (110) is configured for removable insertion into a corresponding strip receiving chamber (46) of rotatable member (44). Each tissue sample strip (110) comprises a set of strip sidewalls (112) joined by a floor (114). Strip sidewalls (112) and floor (114) cooperate to define a tissue receiving chamber (120), such that each tissue sample strip (110) is configured to receive a corresponding tissue sample. Floor (114) defines a plurality of openings (116) that are sized to provide communication of suction and fluids therethrough, while preventing communication of tissue samples therethrough. It should be understood that suction may be communicated through strip receiving chambers (46) to reach tissue receiving chambers (120) via openings (116). Each tissue sample strip (110) of the present example also includes a distal opening (122). Distal opening (122) is sized and configured to enable a severed tissue sample to pass therethrough in order for the tissue sample to be deposited into tissue receiving chamber (120).

Figure 3:
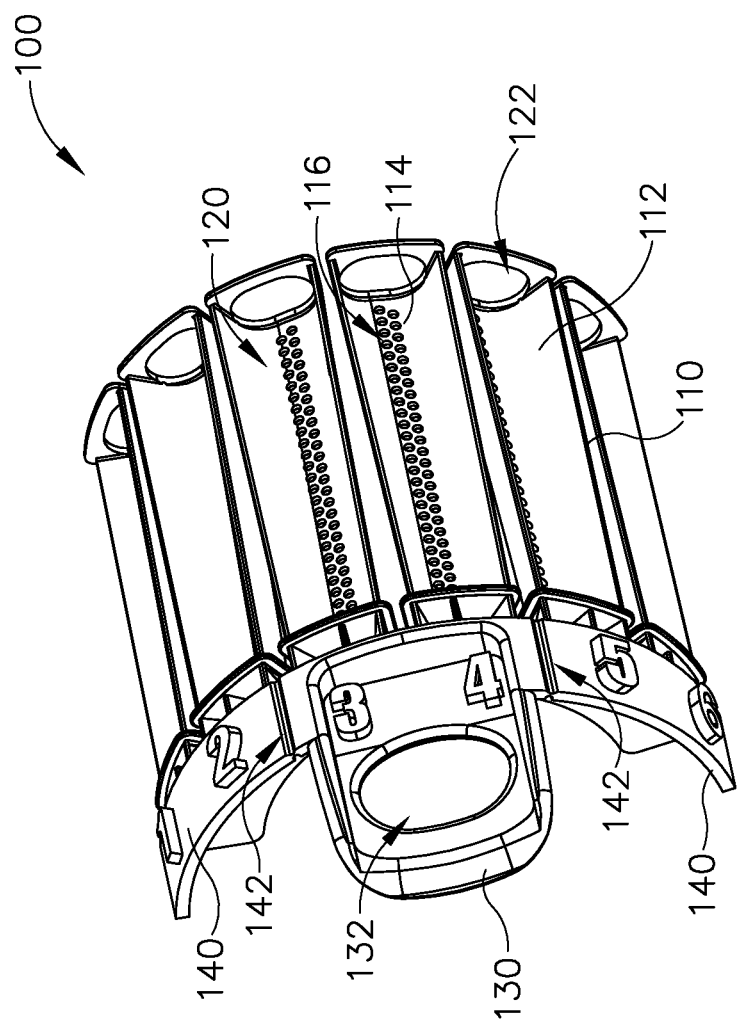
FIG. 3 depicts a perspective view of a tissue sample tray of the tissue sample holder assembly of FIG. 2, with the tissue sample tray in an arcuate configuration.
Figure 4:
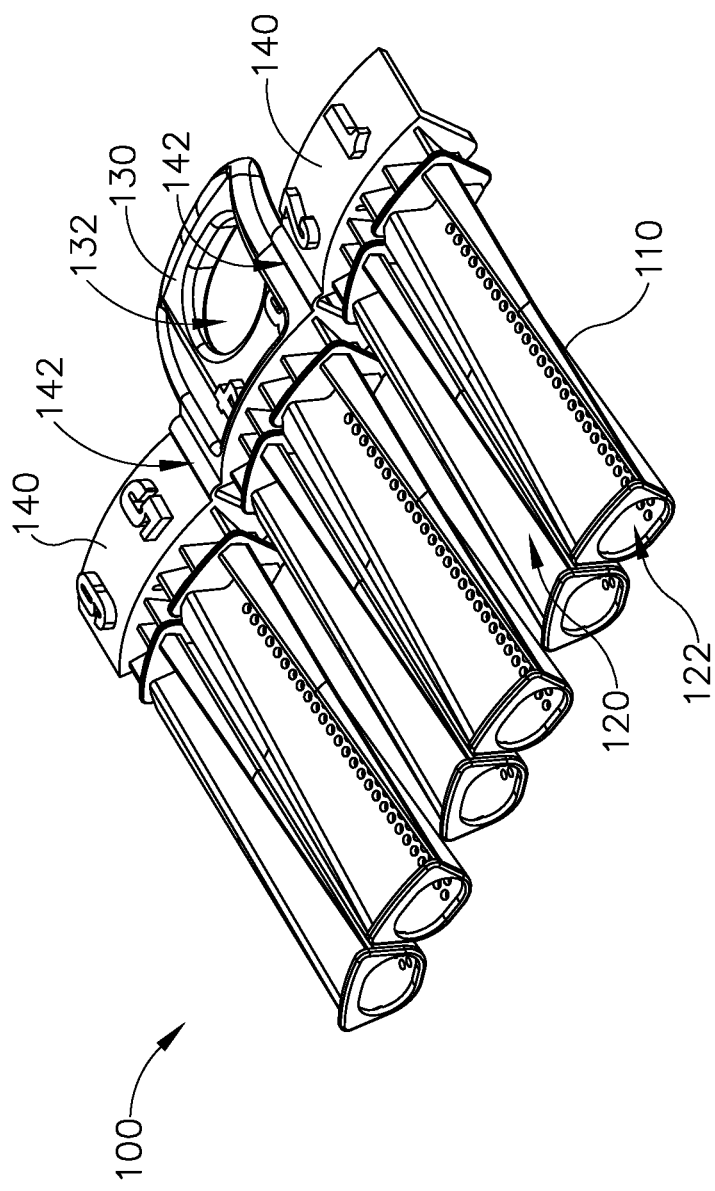
FIG. 4 depicts a perspective view of the tissue sample tray of FIG. 3 in a flattened configuration.

As best seen in FIGS. 3-4, each tissue sample tray (100) further includes a proximally projecting pull tab (130) that defines a tab opening (132). Pull tab (130) is configured to facilitate grasping of tissue sample tray (100) by an operator. Tissue sample tray (100) also includes a set of proximal panels (140). In the present example, two tissue sample strips (110) project distally relative to a corresponding panel (140) of the set of panels (140). Pull tab (130) projects proximally from the centrally positioned panel (140). Panels (140) are flexibly joined together by living hinges (142). Living hinges (142) enable tissue sample tray (100) to transition between the arcuate configuration shown in FIG. 3 and the flattened configuration shown in FIG. 4. In the arcuate configuration, tissue sample tray (100) is configured to fit in rotatable member (44). In the flattened configuration, tissue sample tray (100) is configured to fit in a container (200) as will be described in greater detail below.

As noted above, rotatable member (44) is rotatable relative to probe assembly (20) to selectively index strip receiving chambers (46) relative to the cutter, to thereby selectively index tissue receiving chambers (120) of tissue sample strips (110) relative to the cutter. Rotatable member (44) is also operable to index plug receiving chamber (48) relative to the cutter. When rotatable member (44) is angularly positioned to index plug receiving chamber (48) relative to the cutter, plug (50) may be removed from plug receiving chamber (48) to enable insertion of a biopsy site marker applier instrument (or some other kind of instrument) through the cutter and needle assembly (22), thereby providing an access path to the biopsy site via lateral aperture (26). Otherwise, plug (50) may be left in plug receiving chamber (48) during operation of biopsy device (10), thereby sealing plug receiving chamber (48).

By way of example only, tissue sample holder (40) may be configured and operable in accordance with at least some of the teachings of U.S. Pub. No. 2014/0039343, entitled "Biopsy System," published Feb. 6, 2014, the disclosure of which is incorporated by reference herein and/or U.S. Pub. No. 2014/0275999, entitled "Biopsy Device," published Sep. 18, 2014, the disclosure of which is incorporated by reference herein.

II. Exemplary Container to Support Tissue Sample Tray

As noted above, tissue sample tray (100) is flexible such that tissue sample tray (100) may readily transition between the arcuate configuration shown in FIG. 3 and the flattened configuration shown in FIG. 4. While this flexibility may be beneficial to enable an operator to selectively change the configuration of tissue sample tray (100) based on the needs at hand, this flexibility may also provide a need to provide structural support to tissue sample tray (100) in order to maintain the positioning and arrangement of tissue sample strips (110) based on how tissue sample tray (100) will be handled.

In addition, while the "U"-shaped profile provided by strip sidewalls (112) and floor (114) may enable an operator to easily pull tissue samples from each tissue receiving chamber (120) (i.e., via the opening defined between sidewalls (112)), it may be desirable to provide temporary enclosure of each tissue receiving chamber (120) to fully contain tissue samples in respective tissue receiving chambers (120), particularly when tissue sample tray (100) is in the flattened configuration shown in FIG. 4.

By way of example only, it may be desirable to provide the above-described additional structural support to tissue sample tray (100), as well as the enclosure of each tissue receiving chamber (120) to fully contain tissue samples in respective tissue receiving chambers (120), when the tissue samples are to be positioned in an imaging machine such as a radiograph machine. Similarly, it may be desirable to provide the above-described additional structural support to tissue sample tray (100), as well as the enclosure of each tissue receiving chamber (120) to fully contain tissue samples in respective tissue receiving chambers (120), when the tissue samples are to be contained in a fixation fluid (e.g., formalin).

Figure 7:
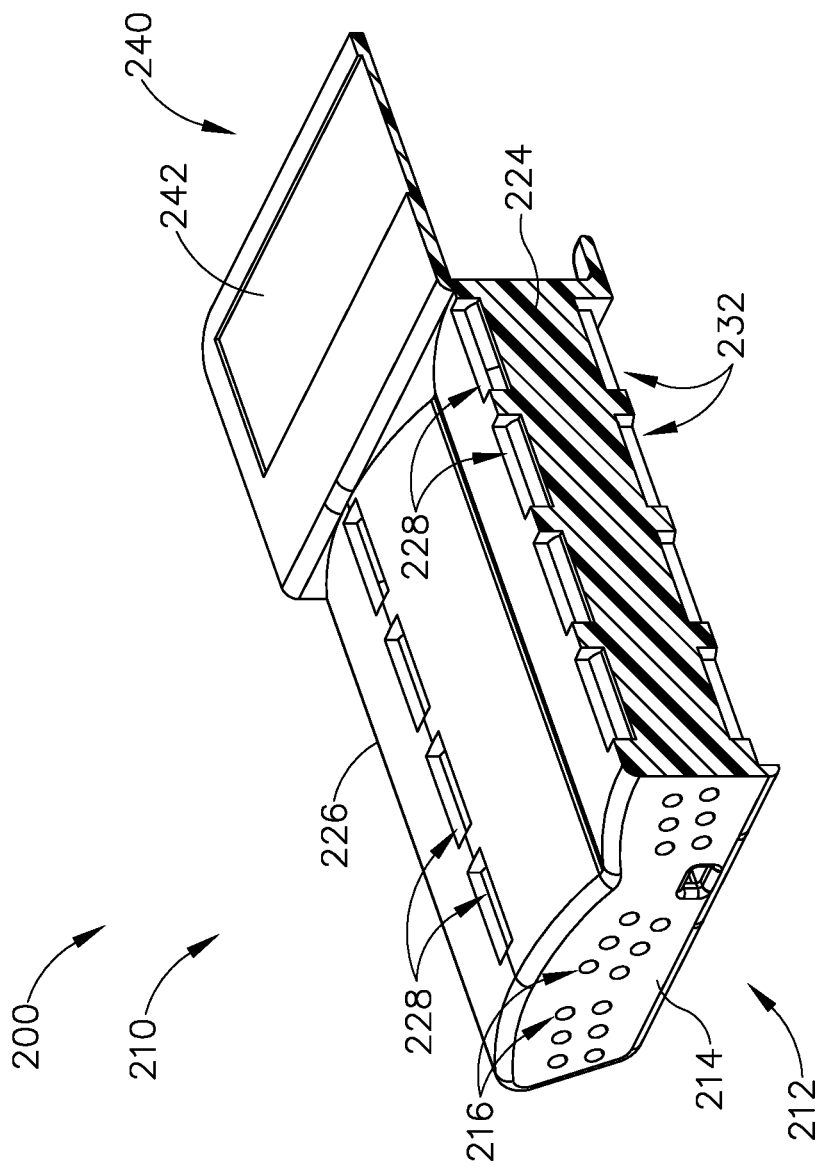
FIG. 7 depicts a perspective cross-sectional view of the container of FIG. 5, with the cross-section taken along line 7-7 of FIG. 5.

FIGS. 5-7 show an exemplary container (200) that is operable to provide structural support to tissue sample tray (100), as well as the enclosure of each tissue receiving chamber (120) to fully contain tissue samples in respective tissue receiving chambers (120). Container (200) of this example comprises a body (210) that defines a plurality of tray receiving portions (212). As will be described in greater detail below, container (200) is generally configured to slidably receive tissue sample tray (100) therein to support and enclose at least a portion of tissue sample tray (100). As will also be described in greater detail below, container (200) of the present example is generally in a rigid flat configuration such that tissue sample tray (100) is correspondingly supported in the flat configuration described above. It should be understood that although container (200) is described herein as being generally rigid, in some example various components of container (200) can be configured to flex or otherwise move to support transitioning of tissue sample tray (100) to the arcuate configuration while still remaining supported by container (200). Suitable examples of flexible components of container (200) will be described in greater detail below.

Body (210) of the present example includes three separate but integrally connected tray receiving portions (212). Tray receiving portions (212) are generally configured to receive a portion of tissue sample tray (100) to support and enclose a portion of tissue receiving tray (100). In particular, and as will be described in greater detail below, each tray receiving portion (212) is configured to receive a pair of tissue samples strips (110) of tissue sample tray (100). Each tray receiving portion (212) comprises a distal end (214), a proximal end (218), a pair of sidewalls (222), a central wall (224), a top (226), and a floor (230). As will be described in greater detail below distal end (214), proximal end (218), sidewalls (222), central wall (224), top (226), and floor (230) all collectively define a pair of tray chambers (234).

As is best seen in FIG. 5, each distal end (214) of each tray receiving portion (212) is integral with a corresponding adjacent distal end (214) such that distal ends (214) define a single distal end (214) extending laterally across body (210). Although distal ends (214) of the present example are shown as being integrally connected, it should be understood that in other examples, distal ends (214) can be separate components secured together at specific points. Regardless, each distal end (214) includes a plurality of vent openings (216). As will be described in greater detail below, vent openings (216) are configured to permit fluid to flow through each distal end (214) and into and out of tray chambers (234).

Sidewalls (222), central wall (224), top (226), and floor (230) all extend proximally from distal end (214) to proximal end (218). Proximal end (218) generally defines a pair of tray openings (220). Tray openings (220) are generally open to tray chambers (234). Thus, it should be understood that each tray opening (220) is configured to receive a corresponding tissue sample strip (110) of tissue sample tray (100) to permit at least a portion of each tissue sample strip (110) to be received within tray chambers (234).

Between distal end (214) and proximal end (218), each top (226) and floor (230) defines a plurality of vent openings (228, 232). Each vent opening (228, 232) is generally configured in a longitudinally elongate configuration. However, it should be understood that in other examples, any other suitable configuration can be used. For instance, in some examples, vent openings (228, 232) may take the form of vent openings (216) associated with distal end (214) (e.g., plurality of oval-shaped or circular openings). Of course, any other suitable shape may be used as will be apparent to those of ordinary skill in the art in view of the teachings herein.

Vent openings (228, 232) of the present example are each configured to communicate between the exterior of container (200) and each tray chamber (234) of each tray receiving portion (212). As is best seen in FIG. 7, each vent opening (228, 232) is directly adjacent to central wall (224) such that a single vent opening (228, 232) is configured to communicate with both tray chambers (234) despite the presence of central wall (224). It should be understood that this configuration permits vent openings (228, 232) to generally occupy less space while maximizing functionality. Of course, in other examples vent openings (228, 232) can be oriented such that a single vent opening (228, 232) communicates with only a single tray chamber (234). It should be understood, however, that in examples of this configuration additional vent openings (228, 232) beyond the number shown in the present example may be required to provide comparable venting as vent openings (228, 232) of the present example.

Returning to FIG. 6, sidewalls (222) and central wall (224) of each tray receiving portion (212) together define the lateral extends of each tray chamber (234). In particular, each sidewall (222) is generally at an obtuse angle (instead of vertical) in correspondence with the shape of strip sidewalls (112) of each tissue sample tray (100). Central wall (224) is disposed between each sidewall (112) to thereby define two discrete tray chambers (234) per each tray receiving portion (212). Although sidewalls (222) and central wall (224) are shown in the present example as having certain specific relationships between each other, it should be understood that these relationships are generally dictated by the size and shape of tissue sample strip (110) of tissue sample tray (100). Thus, it should be understood that in other examples, the relationships between sidewalls (222) and central wall (224) can be varied as desired to accommodate trays (100) with differently sized and shaped tissue sample strips (110).

As described above, each tray receiving portion (212) is joined by each distal end (214) being integral with an adjacent distal end (214). In addition, each tray receiving portion (212) in the present example is also connected to an adjacent tray receiving portion (212) by sidewalls (222). In particular, as can be best seen in FIG. 6, each sidewall (222) that is adjacent to another sidewall (222) of an adjacent tray receiving portion (212) is integrally connected to the adjacent sidewall (222). This integral connection between sidewalls (222) provides additional rigidity to container (200) to support tissue sample tray (100) when at least a portion of tissue sample tray (100) is disposed within each tray receiving portion (212). Although sidewalls (222) of the present example are shown as being integrally connected, it should be understood that in other examples sidewalls (222) can be connected to each other in any other suitable way as will be apparent to those of ordinary skill in the art in view of the teachings herein.

Container (200) further comprises a tab (240). Tab (240) of the present example is configured to permit gripping of container (200) and to permit labeling of container (200). In particular, tab (240) extends proximally from proximal end (218) of body (210). Although tab (240) of the present example is shown as extending laterally across the entire length of proximal end (218), it should be understood that in other examples, tab (240) can extend laterally for only a portion of proximal end (218). Similarly, in some examples tab (240) can be positioned on other locations of body (210). For instance, in still other examples tab (240) can be associated with distal end (214) or sidewalls (222). Of course, any other suitable positioning of tab (240) can be used as will be apparent to those of ordinary skill in the art in view of the teachings herein.

Tab (240) of the present example includes a label portion (242) disposed in the center of an upwardly facing surface of tab (240). Label portion (242) is configured to receive a label therein. As will be described in greater detail below, it may be desirable to label container (200) during various points of a biopsy acquisition and sample analysis procedure. Such labeling may be desirable to promote tracking of tissue samples throughout the procedure.

In the present example, label portion (242) is slightly recessed below the upper surface of tab (240). Accordingly, it should be understood that in the present example label portion (242) is configured to receive a label such that the label will be generally flush with the upper surface of tab (240) once adhered to label portion (242). Although label portion (242) is generally recessed in the present example, it should be understood that in other examples label portion (242) can be configured differently. For instance, in some examples label portion (242) can be a painted surface such that a label may be printed or written directly onto label portion (242) rather than applying a label to label portion (242).

Figure 8:
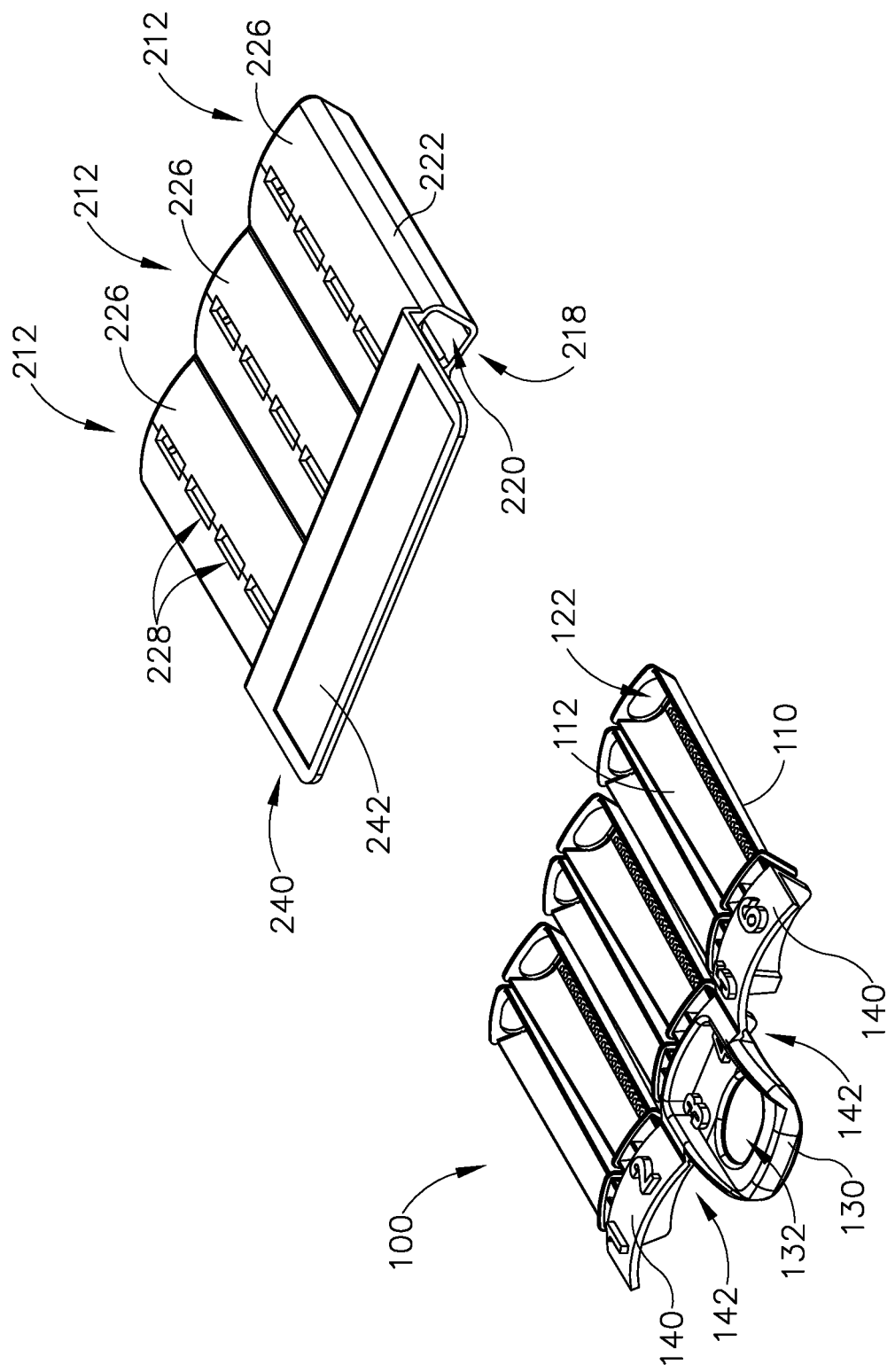
FIG. 8 depicts still another perspective view of the container of FIG. 5, with the tray of FIG. 3 disposed adjacent to the container.

FIGS. 8-12 shown an exemplary use of container (200) to receive tissue sample tray (100). In particular, as can be seen in FIG. 8, tissue sample tray (100) initially begins outside of container (200). It should be understood that in a biopsy procedure, this initial position of tissue sample tray (100) may correspond to point at which tray has received samples from biopsy device (10) and been removed from rotatable member (44) of tissue sample holder assembly (40). Thus, it should be understood that the procedure described herein may be used to prepare tissue sample tray (100) for post-tissue acquisition specimen radiograph followed by subsequent transport of tissue sample tray (100) to pathology for further analysis.

Figure 9:
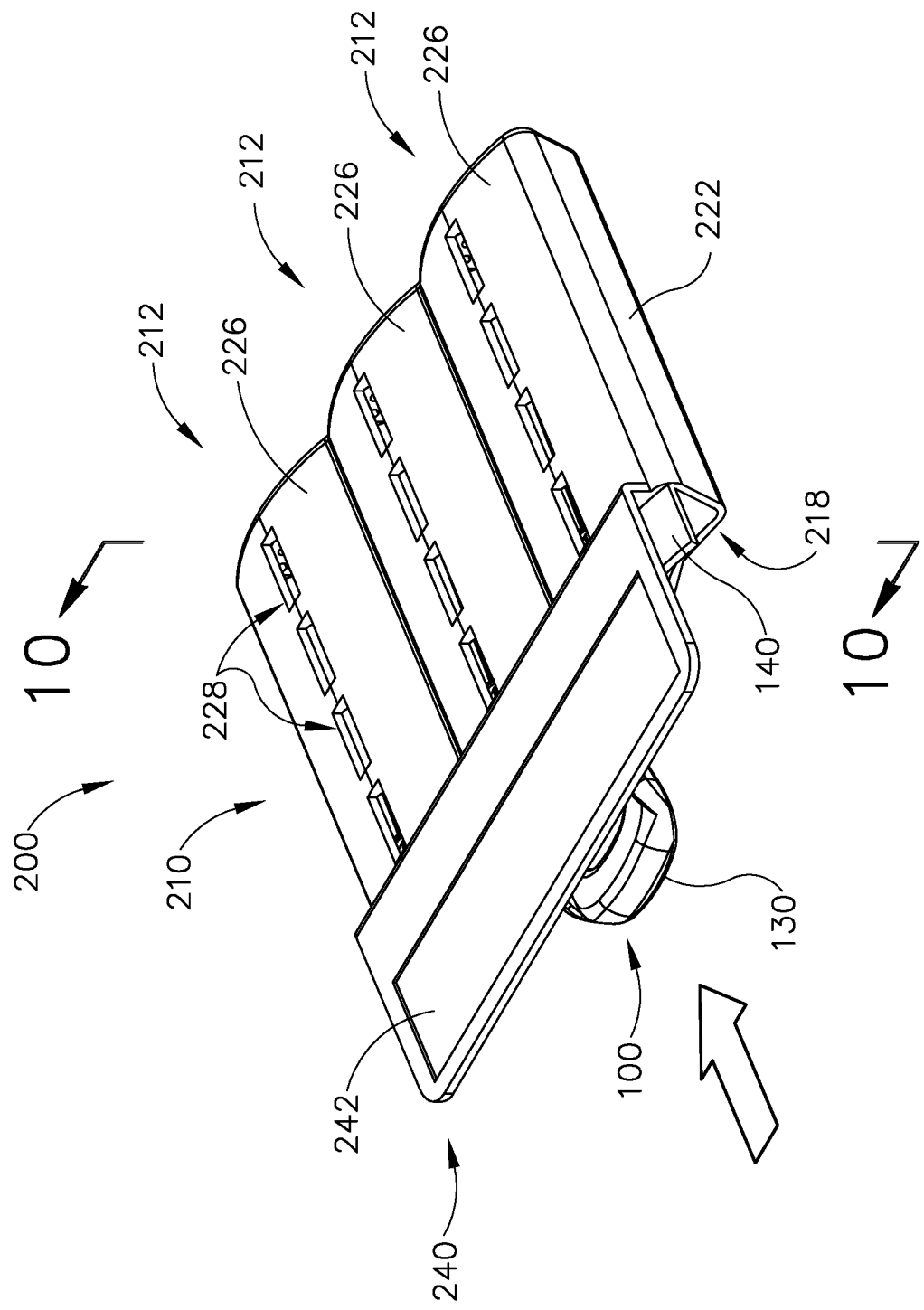
FIG. 9 depicts yet another perspective view of the container of FIG. 5, with at least a portion of the tray of FIG. 3 disposed within the container.

Once tissue sample tray (100) is positioned adjacent to container (200) as shown in FIG. 8, tissue sample tray (100) may be inserted into container into the position shown in FIG. 9. To insert tissue sample tray (100) into container (200), each tissue sample strip (110) of tissue sample tray (100) is aligned with a corresponding tray chamber (234) of each tray receiving portion (212). Tissue sample tray (100) is then translated to insert each tissue sample strip (110) into a corresponding tray chamber (234).

Figure 10:
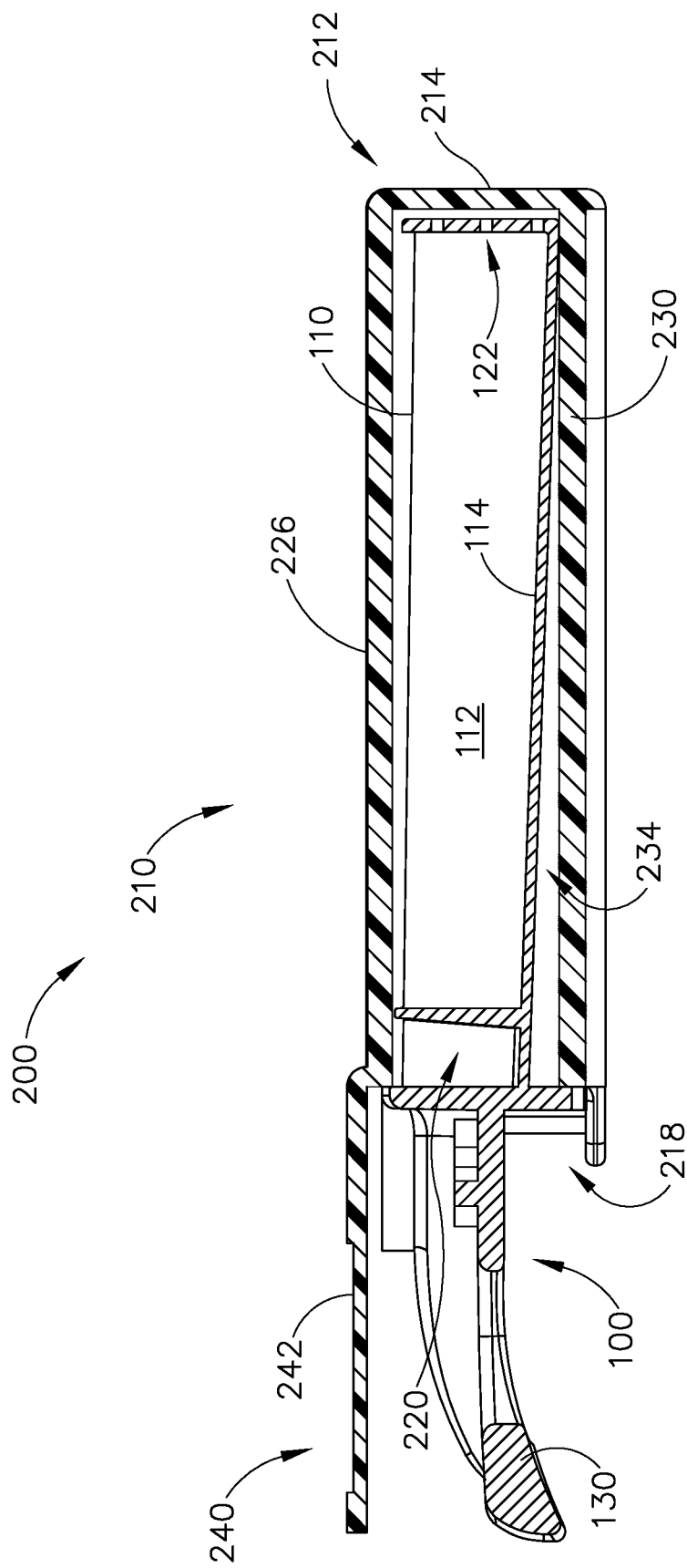
FIG. 10 depicts a side cross-sectional view of the tray of FIG. 3 disposed within the container of FIG. 5, the cross-section taken along line 10-10 of FIG. 9.

As best seen in FIG. 10, once each tissue sample strip (110) of tissue sample tray (100) is inserted into each tray chamber (234) of each tray receiving portion (212), each tissue sample strip (110) is disposed almost entirely within each tray chamber (234). However, each tissue receiving chamber (120) of each tissue sample strip (110) remains in communication with the exterior of container (200) via vent openings (216, 228, 232). In particular, vent openings (216) associated with distal end (214) are in communication with tissue receiving chamber (120) via distal opening (122). Similarly, vent openings (228) associated with top (226) communicate directly with tissue receiving chamber (120), while vent openings (234) associated with floor (232) communicate with tissue receiving chamber (120) via openings (116) in floor (114).

Figure 11:
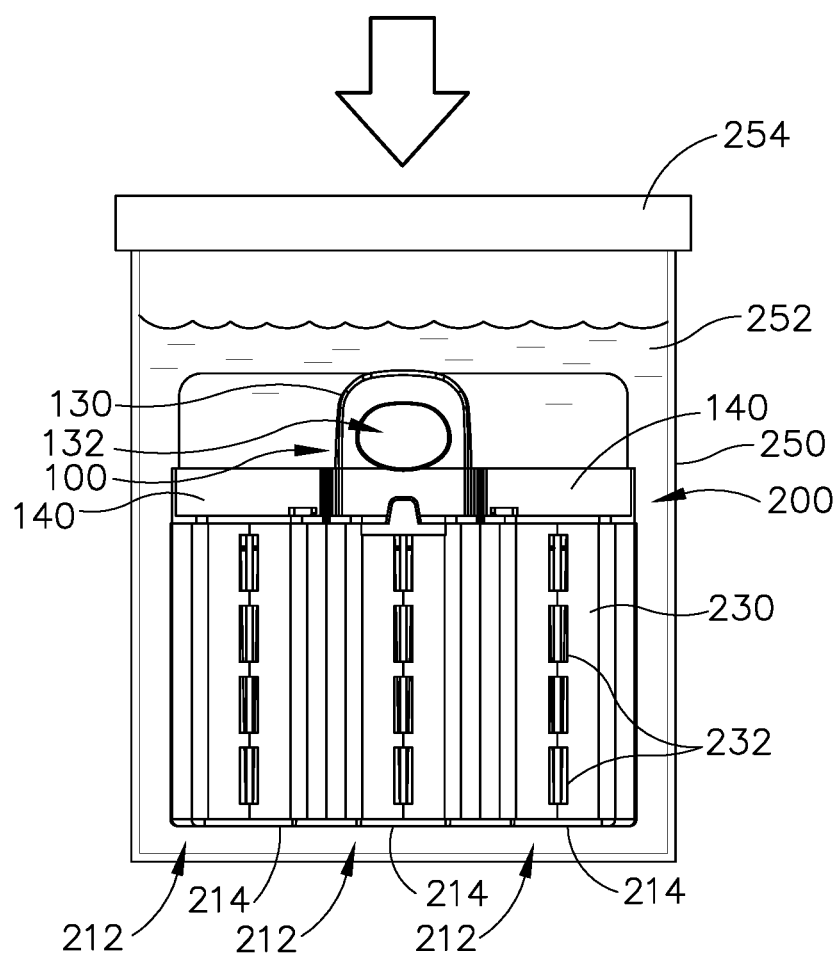
FIG. 11 depicts a front elevational view of the container of FIG. 5 and the tray of FIG. 3 disposed within a cup.

Once each tissue sample strip (110) of tissue sample tray (100) is inserted into a corresponding tray chamber (234) of each tray receiving portion (212), container (200) along with tissue sample tray (100) may be subjected to specimen radiograph, if specimen radiograph is desired. By way of example only, a suitable specimen radiograph procedure may be performed in accordance with at least some of the teachings of U.S. Ser. No. 15/638,740, entitled "Biopsy Sample Container," filed on Jun. 30, 2017, the disclosure of which is incorporated by reference herein. Once specimen radiograph is complete, or if no specimen radiograph is performed, container (200) along with tissue sample tray (100) may be inserted into a cup (250) as shown in FIG. 11. Cup (250) may be used to transport tissue samples such as to a pathology lab. In some instances, cup (250) may be pre-filled with a fixation fluid (252) (e.g., formalin), such that container (200) is immediately immersed in fixation fluid (252). In some other instances, fixation fluid (252) may be introduced to cup (250) after container (200) is first placed in cup (250). In either case, it should be understood that fixation fluid (252) may immediately pass into the interior of container (200) via vent openings (216, 228, 232). Fixation fluid (252) may thereby readily reach and immerse the tissue samples contained within tray chambers (234) in container (200). With container (200) and fixation fluid (252) in cup (250), the operator may then secure cup lid (254) to cup (250), thereby sealing container (200) and fixation fluid (252) in cup (250). After container (200) and fixation fluid (252) are sealed in cup (250), cup (250) may then be transported to another location for further processing, be set aside for storage, or be otherwise handled.

Figure 12:
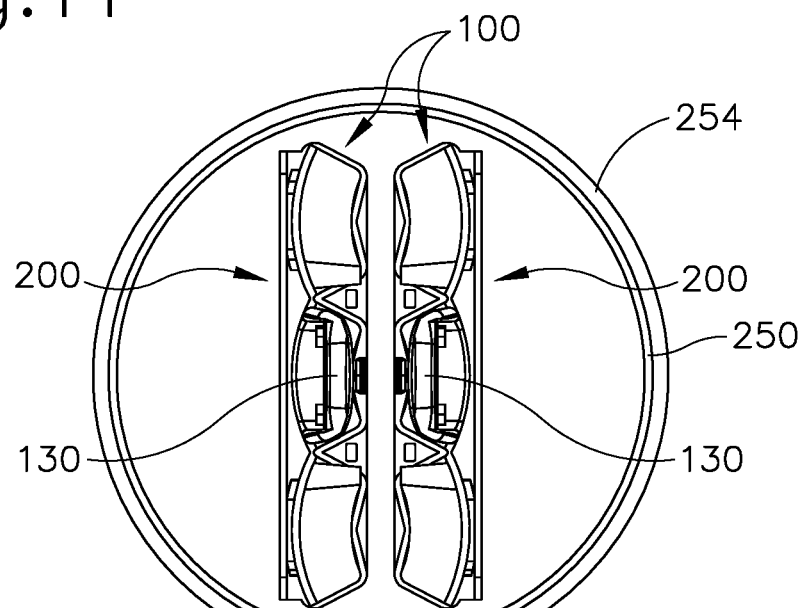
FIG. 12 depicts a top plan view of the container of FIG. 5 and the tray of FIG. 3 disposed within cup of FIG. 11.

As best seen in FIG. 12, it should be understood that in some examples cup (250) may receive multiple containers (200). In particular, in the present example the lateral width of container (200) approximately corresponds to a predetermined dimension less than inner diameter of cup (250). Because of this, it should be understood that lateral width of container (200) is configured such that up to two containers (200) may be disposed within cup (250) at a time.

It should be understood that at any stage during the above referenced procedure, a label may be affixed to label portion (242) of tab (240). For instance, instance in some examples a label may be attached or otherwise provided on label portion (242) prior to insertion of tissue sample tray (100) into container (200). In other examples, a label may be attached or otherwise provided on label portion (242) after insertion of tissue sample tray (100) into container (200). Of course, in still other examples a label may be attached or otherwise provided on label portion (242) at any other suitable point during the above described procedure.

III. Exemplary Alternative Containers to Support Tissue Sample Tray

Figure 13:
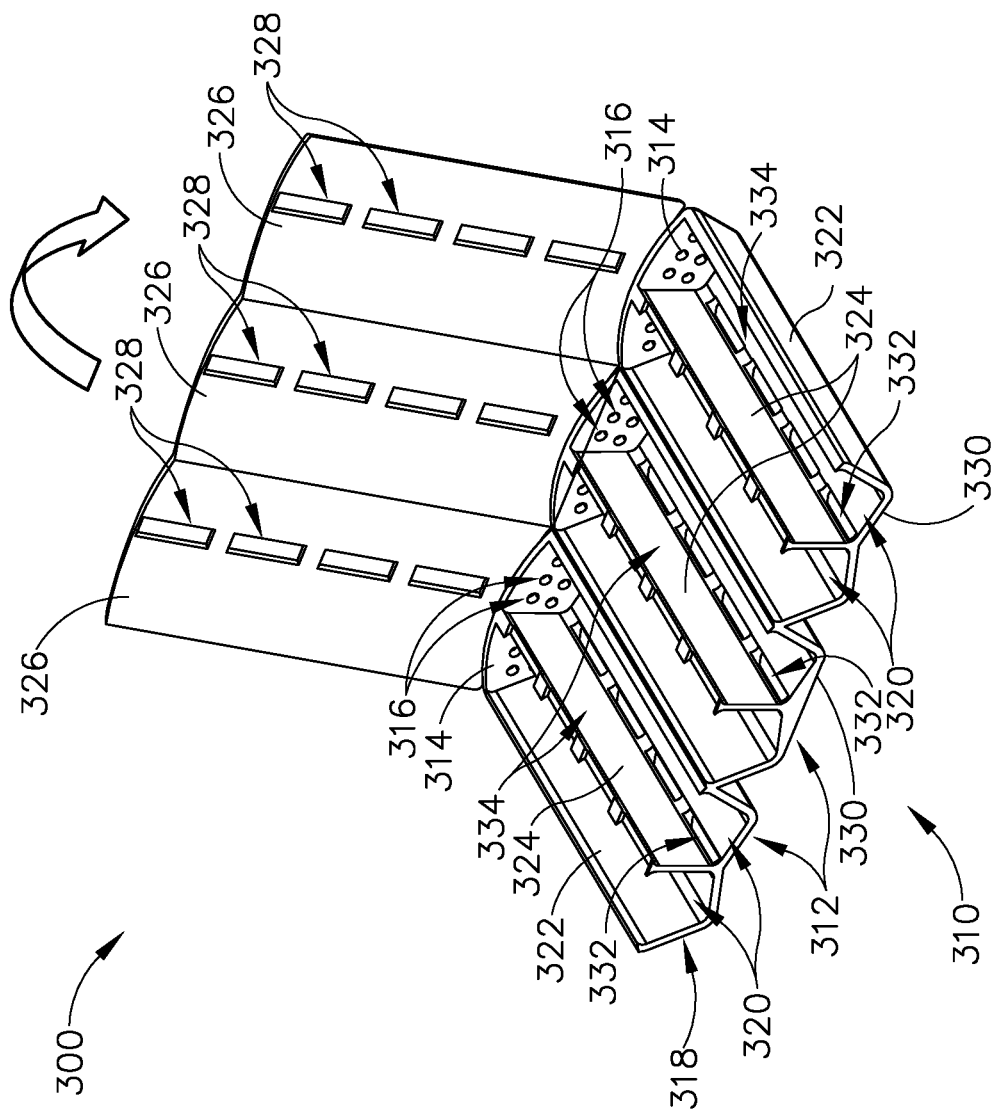
FIG. 13 depicts a perspective view of an exemplary alternative container for use with the tray of FIG. 3.

FIG. 13 shows an exemplary alternative container (300) that is substantially similar to container (200) described above. For instance, like with container (200), container (300) is operable to provide structural support to tissue sample tray (100), as well as the enclosure of each tissue receiving chamber (120) to fully contain tissue samples in respective tissue receiving chambers (120). However, unlike container (200) described above, container (300) of the present example is generally configured to receive tissue sample tray (100) in a drop-in fashion in addition to slidably receiving tissue sample tray (100). Container (300) of this example comprises a body (310) that defines a plurality of tray receiving portions (312). As will be described in greater detail below, container (300) is generally configured to slidably receive tissue sample tray (100) therein to support and enclose at least a portion of tissue sample tray (100). As will also be described in greater detail below, container (300) of the present example is generally in a rigid flat configuration such that tissue sample tray (100) is correspondingly supported in the flat configuration described above.

Body (310) of the present example includes three separate but integrally connected tray receiving portions (312). Tray receiving portions (312) are generally configured to receive a portion of tissue sample tray (100) to support and enclose a portion of tissue receiving tray (100). In particular, and as will be described in greater detail below, each tray receiving portion (312) is configured to receive a pair of tissue samples strips (110) of tissue sample tray (100). Each tray receiving portion (312) comprises a distal end (314), a proximal end (318), a pair of sidewalls (322), a central wall (324), a top (326), and a floor (330). As will be described in greater detail below distal end (314), proximal end (318), sidewalls (322), central wall (324), top (326), and floor (330) all collectively define a pair of tray chambers (334).

Each distal end (314) of each tray receiving portion (312) is integral with a corresponding adjacent distal end (314) such that distal ends (314) define a single distal end (314)

extending laterally across body (310). Although distal ends (314) of the present example are shown as being integrally connected, it should be understood that in other examples, distal ends (314) can be separate components secured together at specific points. Regardless, each distal end (314) includes a plurality of vent openings (316). Like with vent openings (216) described above, vent openings (316) of the present example are configured to permit fluid to flow through each distal end (314) and into and out of tray chambers (334).

Sidewalls (322), central wall (324), top (326), and floor (330) all extend proximally from distal end (314) to proximal end (318). Proximal end (318) generally defines a pair of tray openings (320). Tray openings (320) are generally open to tray chambers (334). Thus, it should be understood that each tray opening (320) is configured to receive a corresponding tissue sample strip (110) of tissue sample tray (100) to permit at least a portion of each tissue sample strip (110) to be received within tray chambers (334).

Between distal end (314) and proximal end (318), each top (326) and floor (330) defines a plurality of vent openings (328, 332). Each vent opening (328, 332) is generally configured in a longitudinally elongate configuration. However, it should be understood that in other examples, any other suitable configuration can be used. For instance, in some examples, vent openings (328, 332) may take the form of vent openings (316) associated with distal end (314) (e.g., plurality of oval-shaped or circular openings). Of course, any other suitable shape may be used as will be apparent to those of ordinary skill in the art in view of the teachings herein.

Vent openings (328, 332) of the present example are each configured to communicate between the exterior of container (300) and each tray chamber (334) of each tray receiving portion (312). Each vent opening (328, 332) is directly adjacent to central wall (324) such that a single vent opening (328, 332) is configured to communicate with both tray chambers (334) despite the presence of central wall (324).

Sidewalls (322) and central wall (324) of each tray receiving portion (312) together define the lateral extends of each tray chamber (334). In particular, each sidewall (322) is generally at an obtuse angle (instead of vertical) in correspondence with the shape of strip sidewalls (112) of each tissue sample tray (100). Central wall (324) is disposed between each sidewall (112) to thereby define two discrete tray chambers (334) per each tray receiving portion (312). Although sidewalls (322) and central wall (324) are shown in the present example as having certain specific relationships between each other, it should be understood that these relationships are generally dictated by the size and shape of tissue sample strip (110) of tissue sample tray (100). Thus, it should be understood that in other examples, the relationships between sidewalls (322) and central wall (324) can be varied as desired to accommodate trays (100) with differently sized and shaped tissue sample strips (110).

As described above, each tray receiving portion (312) is joined by each distal end (314) being integral with an adjacent distal end (314). In addition, each tray receiving portion (312) in the present example is also connected to an adjacent tray receiving portion (312) by sidewalls (322). Each sidewall (322) that is adjacent to another sidewall (322) of an adjacent tray receiving portion (312) is integrally connected to the adjacent sidewall (322). This integral connection between sidewalls (322) provides additional rigidity to container (300) to support tissue sample tray (100) when at least a portion of tissue sample tray (100) is disposed within each tray receiving portion (312).

Unlike container (200), container (300) of the present example is not shown as including a tab similar to tab (240) described above. However, although not shown, it should be understood that in some examples container (300) can include a tab similar to tab (240) described above. In such examples, such a tab can be configured to permit gripping of container (300) and to permit labeling of container (300). Additionally, such a tab may likewise include a label portion similar to label portion (242) described above. Such a label portion can be recessed such that it is configured to receive a label therein.

Unlike container (200) described above, container (300) of the present example is configured such that at least a portion of each top (326) of each tray receiving portion (312) is removable from the rest of body (310). In particular, as can be seen in FIG. 13, each top (326) is interconnected with each other such that all tops (326) can be pivoted away from body (310) to open body (310). This feature is configured to provide additional functionality such that tissue sample tray (100) can be inserted into container (300) by sliding or by dropping through the open area defined by tops (326) when pivoted.

Although not shown, it should be understood that in the present example each top (326) is secured to body (310) by a living hinge connecting the proximal end of each top to proximal end (318) of each tray receiving portion (312). Although a living hinge feature is described in connection with the present example, it should be understood that in other examples any other suitable hinge feature may be used. In still other examples, the living hinge may be omitted entirely and each top (326) may be fully removable from body (310). In addition, although the present example is shown as only having removable tops (326), it should be understood that in other examples, portions of sidewalls (322) and central walls (324) can also be removable with tops (326).

Figure 14:
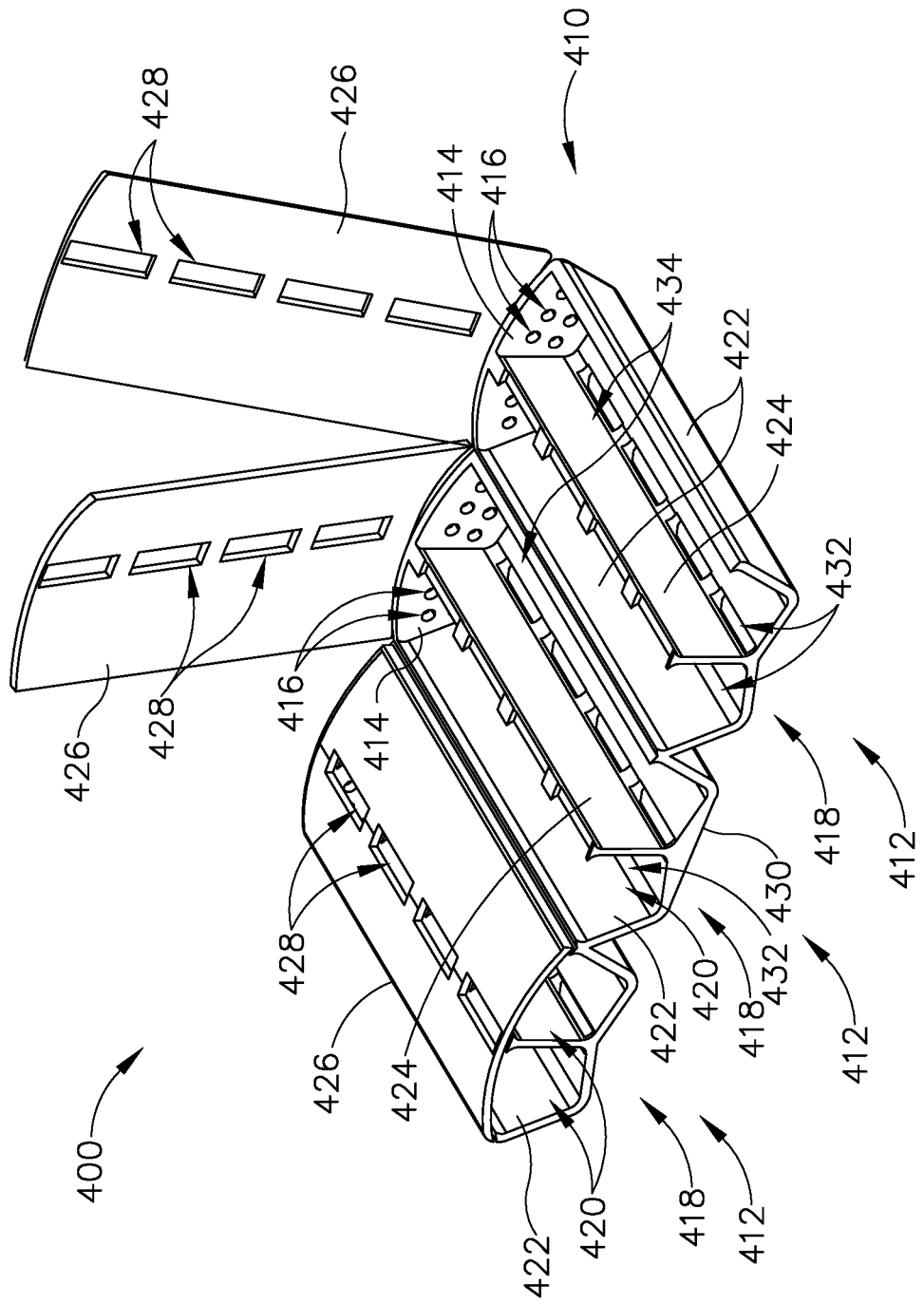
FIG. 14 depicts a perspective view of another exemplary alternative container for use with the tray of FIG. 3.

FIG. 14 shows an exemplary alternative container (400) that is substantially similar to container (300) described above. For instance, like with container (300), container (400) is operable to provide structural support to tissue sample tray (100), as well as the enclosure of each tissue receiving chamber (120) to fully contain tissue samples in respective tissue receiving chambers (120). Container (400) of this example comprises a body (410) that defines a plurality of tray receiving portions (412). As will be described in greater detail below, container (400) is generally configured to slidably receive tissue sample tray (100) therein to support and enclose at least a portion of tissue sample tray (100).

Body (410) of the present example includes three separate but integrally connected tray receiving portions (412). Tray receiving portions (412) are generally configured to receive a portion of tissue sample tray (100) to support and enclose a portion of tissue receiving tray (100). In particular, and as will be described in greater detail below, each tray receiving portion (412) is configured to receive a pair of tissue samples strips (110) of tissue sample tray (100). Each tray receiving portion (412) comprises a distal end (414), a proximal end (418), a pair of sidewalls (422), a central wall (424), a top (426), and a floor (430). As will be described in greater detail below distal end (414), proximal end (418), sidewalls (422), central wall (424), top (426), and floor (430) all collectively define a pair of tray chambers (434).

Each distal end (414) of each tray receiving portion (412) is integral with a corresponding adjacent distal end (414)

such that distal ends (414) define a single distal end (414) extending laterally across body (410). Although distal ends (414) of the present example are shown as being integrally connected, it should be understood that in other examples, distal ends (414) can be separate components secured together at specific points. Regardless, each distal end (414) includes a plurality of vent openings (416). Like with vent openings (316) described above, vent openings (416) of the present example are configured to permit fluid to flow through each distal end (414) and into and out of tray chambers (434).

Sidewalls (422), central wall (424), top (426), and floor (430) all extend proximally from distal end (414) to proximal end (418). Proximal end (418) generally defines a pair of tray openings (420). Tray openings (420) are generally open to tray chambers (434). Thus, it should be understood that each tray opening (420) is configured to receive a corresponding tissue sample strip (110) of tissue sample tray (100) to permit at least a portion of each tissue sample strip (110) to be received within tray chambers (434).

Between distal end (414) and proximal end (418), each top (426) and floor (430) defines a plurality of vent openings (428, 432). Each vent opening (428, 432) is generally configured in a longitudinally elongate configuration. However, it should be understood that in other examples, any other suitable configuration can be used. For instance, in some examples, vent openings (428, 432) may take the form of vent openings (416) associated with distal end (414) (e.g., plurality of oval-shaped or circular openings). Of course, any other suitable shape may be used as will be apparent to those of ordinary skill in the art in view of the teachings herein.

Vent openings (428, 432) of the present example are each configured to communicate between the exterior of container (400) and each tray chamber (434) of each tray receiving portion (412). Each vent opening (428, 432) is directly adjacent to central wall (424) such that a single vent opening (428, 432) is configured to communicate with both tray chambers (434) despite the presence of central wall (424).

Sidewalls (422) and central wall (424) of each tray receiving portion (412) together define the lateral extends of each tray chamber (434). In particular, each sidewall (422) is generally at an obtuse angle (instead of vertical) in correspondence with the shape of strip sidewalls (112) of each tissue sample tray (100). Central wall (424) is disposed between each sidewall (112) to thereby define two discrete tray chambers (434) per each tray receiving portion (412). Although sidewalls (422) and central wall (424) are shown in the present example as having certain specific relationships between each other, it should be understood that these relationships are generally dictated by the size and shape of tissue sample strip (110) of tissue sample tray (100). Thus, it should be understood that in other examples, the relationships between sidewalls (422) and central wall (424) can be varied as desired to accommodate trays (100) with differently sized and shaped tissue sample strips (110).

As described above, each tray receiving portion (412) is joined by each distal end (414) being integral with an adjacent distal end (414). In addition, each tray receiving portion (412) in the present example is also connected to an adjacent tray receiving portion (412) by sidewalls (422). Each sidewall (422) that is adjacent to another sidewall (422) of an adjacent tray receiving portion (412) is integrally connected to the adjacent sidewall (422). This integral connection between sidewalls (422) provides additional rigidity to container (400) to support tissue sample tray (100) when at least a portion of tissue sample tray (100) is disposed within each tray receiving portion (412).

Unlike container (200), container (400) of the present example is not shown as including a tab similar to tab (240) described above. However, although not shown, it should be understood that in some examples container (400) can include a tab similar to tab (240) described above. In such examples, such a tab can be configured to permit gripping of container (400) and to permit labeling of container (400). Additionally, such a tab may likewise include a label portion similar to label portion (242) described above. Such a label portion can be recessed such that it is configured to receive a label therein.

Unlike container (200) described above and similarly to container (300), container (400) of the present example is configured such that at least a portion of each top (426) of each tray receiving portion (412) is removable from the rest of body (410). In particular, as can be seen in FIG. 14, each top (426) is configured to be pivoted away from body (410) to open body (410). However, unlike tops (326) of container (300) described above, tops (426) of the present example are not interconnected. Instead, each top (426) is independently pilotable relative to the other tops (426). Thus, each tray receiving portion (412) is configured to be opened independently relative to the other tray receiving portions (412). This feature is configured to provide additional functionality such that tissue sample tray (100) can be inserted into container (400) by sliding or by dropping through the open area defined by tops (426) when tops (426) are pivoted.

Although not shown, it should be understood that in the present example each top (426) is secured to body (410) by a living hinge connecting the proximal end of each top to proximal end (418) of each tray receiving portion (412). Although a living hinge feature is described in connection with the present example, it should be understood that in other examples any other suitable hinge feature may be used. In still other examples, the living hinge may be omitted entirely and each top (426) may be fully removable from body (410). In addition, although the present example is shown as only having removable tops (426), it should be understood that in other examples, portions of sidewalls (422) and central walls (424) can also be removable with tops (426).

Figure 15:
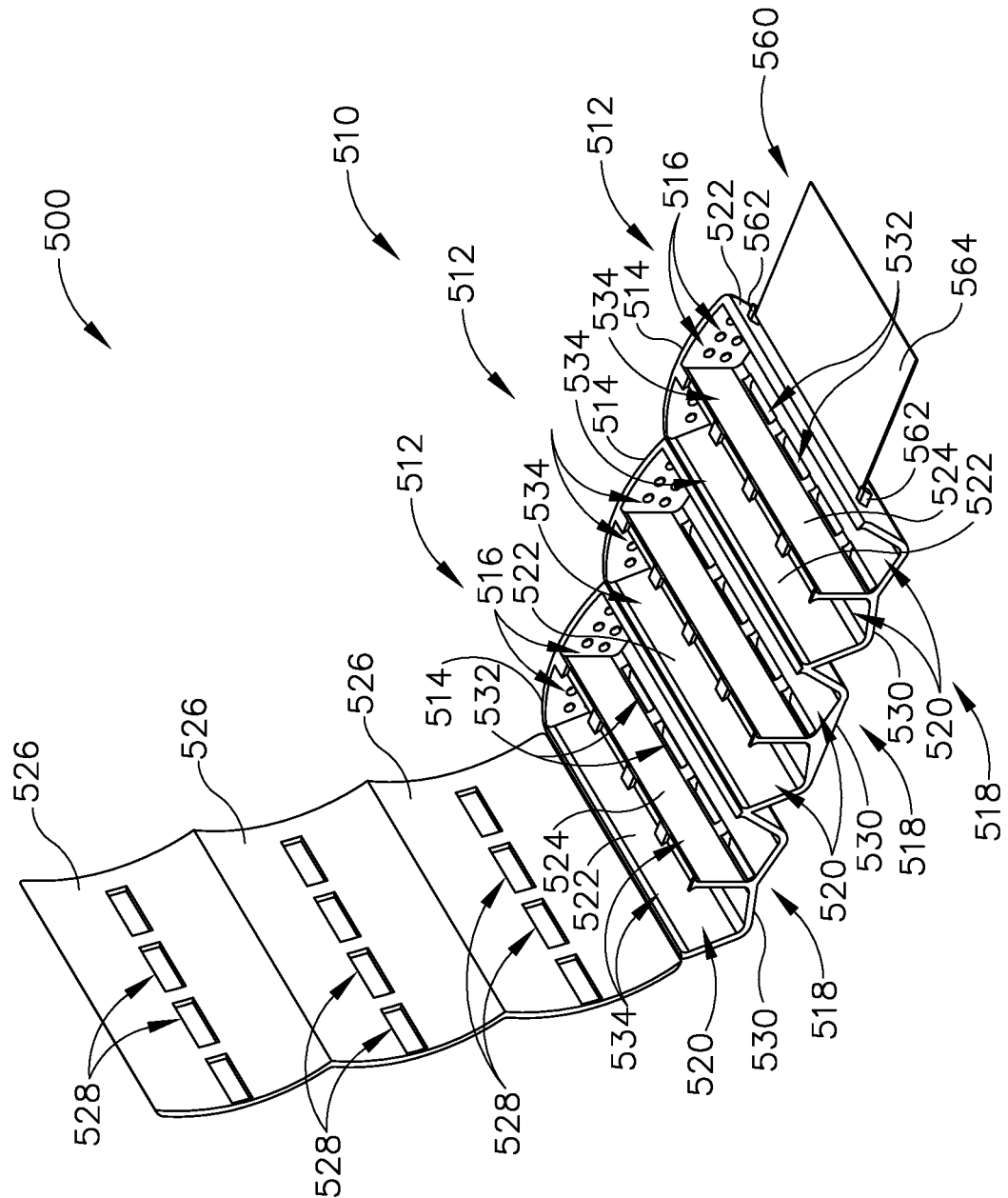
FIG. 15 depicts a perspective view of still another exemplary alternative container for use with the tray of FIG. 3.

FIG. 15 shows an exemplary alternative container (500) that is substantially similar to containers (300, 400) described above. For instance, like with containers (300, 400), container (500) is operable to provide structural support to tissue sample tray (100), as well as the enclosure of each tissue receiving chamber (120) to fully contain tissue samples in respective tissue receiving chambers (120). Container (500) of this example comprises a body (510) that defines a plurality of tray receiving portions (512). As will be described in greater detail below, container (500) is generally configured to slidably receive tissue sample tray (100) therein to support and enclose at least a portion of tissue sample tray (100).

Body (510) of the present example includes three separate but integrally connected tray receiving portions (512). Tray receiving portions (512) are generally configured to receive a portion of tissue sample tray (100) to support and enclose a portion of tissue receiving tray (100). In particular, and as will be described in greater detail below, each tray receiving portion (512) is configured to receive a pair of tissue samples strips (110) of tissue sample tray (100). Each tray receiving portion (512) comprises a distal end (514), a proximal end (518), a pair of sidewalls (522), a central wall (524), a top (526), and a floor (530). As will be described in greater detail below distal end (514), proximal end (518), sidewalls (522), central wall (524), top (526), and floor (530) all collectively define a pair of tray chambers (534).

Each distal end (514) of each tray receiving portion (512) is integral with a corresponding adjacent distal end (514) such that distal ends (514) define a single distal end (514) extending laterally across body (510). Although distal ends (514) of the present example are generally integrally connected, it should be understood that in other examples, distal ends (514) can be separate components secured together at specific points. Regardless, each distal end (514) includes a plurality of vent openings (516). Like with vent openings (316) described above, vent openings (516) of the present example are configured to permit fluid to flow through each distal end (514) and into and out of tray chambers (534).

Sidewalls (522), central wall (524), top (526), and floor (530) all extend proximally from distal end (514) to proximal end (518). Proximal end (518) generally defines a pair of tray openings (520). Tray openings (520) are generally open to tray chambers (534). Thus, it should be understood that each tray opening (520) is configured to receive a corresponding tissue sample strip (110) of tissue sample tray (100) to permit at least a portion of each tissue sample strip (110) to be received within tray chambers (534).

Between distal end (514) and proximal end (518), each top (526) and floor (530) defines a plurality of vent openings (528, 532). Each vent opening (528, 532) is generally configured in a longitudinally elongate configuration. However, it should be understood that in other examples, any other suitable configuration can be used. For instance, in some examples, vent openings (528, 532) may take the form of vent openings (516) associated with distal end (514) (e.g., plurality of oval-shaped or circular openings). Of course, any other suitable shape may be used as will be apparent to those of ordinary skill in the art in view of the teachings herein.

Vent openings (528, 532) of the present example are each configured to communicate between the exterior of container (500) and each tray chamber (534) of each tray receiving portion (512). Each vent opening (528, 532) is directly adjacent to central wall (524) such that a single vent opening (528, 532) is configured to communicate with both tray chambers (534) despite the presence of central wall (524).

Sidewalls (522) and central wall (524) of each tray receiving portion (512) together define the lateral extends of each tray chamber (534). In particular, each sidewall (522) is generally at an obtuse angle (instead of vertical) in correspondence with the shape of strip sidewalls (112) of each tissue sample tray (100). Central wall (524) is disposed between each sidewall (112) to thereby define two discrete tray chambers (534) per each tray receiving portion (512). Although sidewalls (522) and central wall (524) are shown in the present example as having certain specific relationships between each other, it should be understood that these relationships are generally dictated by the size and shape of tissue sample strip (110) of tissue sample tray (100). Thus, it should be understood that in other examples, the relationships between sidewalls (522) and central wall (524) can be varied as desired to accommodate trays (100) with differently sized and shaped tissue sample strips (110).

As described above, each tray receiving portion (512) is joined by each distal end (514) being integral with an adjacent distal end (514). In addition, each tray receiving portion (512) in the present example is also connected to an adjacent tray receiving portion (512) by sidewalls (522). Each sidewall (522) that is adjacent to another sidewall (522) of an adjacent tray receiving portion (512) is integrally connected to the adjacent sidewall (522). This integral connection between sidewalls (522) provides additional rigidity to container (500) to support tissue sample tray (100) when at least a portion of tissue sample tray (100) is disposed within each tray receiving portion (512).

Unlike container (200), container (500) of the present example is not shown as including a tab similar to tab (240) described above. However, although not shown, it should be understood that in some examples container (500) can include a tab similar to tab (240) described above. In such examples, such a tab can be configured to permit gripping of container (500) and to permit labeling of container (500). Additionally, such a tab may likewise include a label portion similar to label portion (242) described above. Such a label portion can be recessed such that it is configured to receive a label therein.

Unlike container (200) described above and similarly to containers (300, 400), container (400) of the present example is configured such that at least a portion of each top (526) of each tray receiving portion (512) is removable from the rest of body (410). In particular, as can be seen in FIG. 15, each top (526) is configured to be pivoted away from body (510) to open body (510). Like tops (326) of container (300) described above, tops (526) of the present example are each interconnected such that tops (526) are pivotable as a discrete unit. Thus, each tray receiving portion (512) is configured to be opened simultaneously with the other tray receiving portions (512). This feature is configured to provide additional functionality such that tissue sample tray (100) can be inserted into container (500) by sliding or by dropping through the open area defined by tops (526) when tops (526) are pivoted.

Although not shown, it should be understood that in the present example each top (526) is secured to body (510) by a living hinge connecting the side of each top (526) a lateral most sidewall (522) of each tray receiving portion (512). Thus it should be understood that unlike containers (300, 400) described above, container (500) of the present example includes a hinge feature that is disposed in a different position. Although a living hinge feature is described in connection with the present example, it should be understood that in other examples any other suitable hinge feature may be used. In still other examples, the living hinge may be omitted entirely and each top (526) may be fully removable from body (510). In addition, although the present example is shown as only having removable tops (526), it should be understood that in other examples, portions of sidewalls (522) and central walls (524) can also be removable with tops (526).

Unlike containers (200, 300, 400) described above, container (500) of the present example further comprises a labeling portion (560) extending laterally from an outer most sidewall (522) of an outer most tray receiving portion (512). Labeling portion (560) of the present example comprises a pair of arms (562) and a label member (564). Arms (562) extend outwardly from sidewall (522) to provide a gap between sidewall (522) and label member (564). Although labeling portion (560) of the present example includes arms (562), it should be understood that in some examples arms (562) may be omitted entirely. In such examples, label member (564) is directly secured to sidewall (522).

Label member (564) extends outwardly from arms (562). Although not shown, it should be understood that in the present example arms (562) include a dowel extending between each arm (562). Label member (564) is rotatably secured to the dowel extending between each arm (562) such that label member (564) is configured to rotate relative to arms (562). Label member (564) is generally flexible such that label member (564) is configured to fold, twist, bend, or otherwise transition between various positions. Accordingly, it should be understood that label member (564) is configured similarly to a flag such that label member (564) may rotate about arms, to fold and bend around container (500). This feature permits label member (564) to transition to a compact position for various scenarios where container (500) is disposed within confined spaces (e.g., when in cup (250) described above).

Label member (564) of the present example is configured to receive labels on an upper or lower surface. For example, in some uses of label member (564) an operator may place a self-adhering label onto label member (564) at various stages during a biopsy and tissue analysis procedure. Although label member (564) of the present example is described in connection with receiving a separate label, it should be understood that in other examples a label may be written or printed directly onto label member (564).

IV. Exemplary Foldable Container to Support Tissue Sample Tray

As noted above, in some circumstances it may be desirable to provide structural support to tissue sample tray (100) in order to maintain the positioning and arrangement of tissue sample strips (110) based on how tissue sample tray (100) will be handled. However, it should be understood that this structural support need not necessarily be isotropic in nature as described above with respect to container (200). By way of example only, it may be desirable to provide the above-described additional structural support to tissue sample tray (100) along a single plane or with respect to a specific portion of tissue sample tray (100). However, it should be understood that in such examples, it may still be desirable to provide enclosure of each tissue receiving chamber (120) to fully contain tissue samples in respective tissue receiving chambers (120), when the tissue samples are to be contained in a fixation fluid (e.g., formalin).

FIGS. 16 and 17 show an exemplary container (600) that is operable to provide structural support to tissue sample tray (100), as well as the enclosure of each tissue receiving chamber (120) to fully contain tissue samples in respective tissue receiving chambers (120). However, unlike container (200) described above, container (600) of the present example is generally bendable across at least one axis to accommodate container (600) within various fluid containing devices, as will be described in greater detail below.

Like with container (200) described above, container (600) of this example comprises a body (610) that defines a plurality of tray receiving portions (612). As will be described in greater detail below, container (600) is generally configured to slidably receive tissue sample tray (100) therein to support and enclose at least a portion of tissue sample tray (100). As will also be described in greater detail below, container (600) of the present example is generally in a rigid, yet each tray receiving portion (612) is pivotable relative to an adjacent tray receiving portion (612) such that container (600) is configured to transition from a flat configuration to an arcuate configuration.

Body (610) of the present example includes three separate but integrally connected tray receiving portions (612). Tray receiving portions (612) are generally configured to receive a portion of tissue sample tray (100) to support and enclose a portion of tissue receiving tray (100). In particular, and as will be described in greater detail below, each tray receiving portion (612) is configured to receive a pair of tissue samples strips (110) of tissue sample tray (100). Each tray receiving portion (612) comprises a distal end (614), a proximal end (618), a pair of sidewalls (622), a central wall (624), a top (626), and a floor (630). As will be described in greater detail below distal end (614), proximal end (618), sidewalls (622), central wall (624), top (626), and floor (630) all collectively define a pair of tray chambers (634).

Each distal end (614) of each tray receiving portion (612) is integral with, yet separate from, a corresponding adjacent distal end (614) such that distal ends (614) are interconnected to extend laterally across body (610). In particular, each distal end (614) is generally interconnected with only a portion of another adjacent distal end (614) to define a gap (670) between each distal end (614). As will be described in greater detail below, this configuration generally permits distal ends (614) to flex relative to each other, thereby permitting each tray receiving portion (612) to transition from the flat configuration to the arcuate configuration.

Each distal end (614) includes a plurality of vent openings (616). Like with vent openings (216) described above, vent openings (616) of the present example are configured to permit fluid to flow through each distal end (614) and into and out of tray chambers (634). As will be described in greater detail below, this configuration permits tray chambers (634) to fill with a fixation fluid (e.g., formalin) to thereby submerge tissue samples in the fixation fluid.

Sidewalls (622), central wall (624), top (626), and floor (630) all extend proximally from distal end (614) to proximal end (618). Proximal end (618) generally defines a pair of tray openings (620). Tray openings (620) are generally open to tray chambers (634). Thus, it should be understood that each tray opening (620) is configured to receive a corresponding tissue sample strip (110) of tissue sample tray (100) to permit at least a portion of each tissue sample strip (110) to be received within tray chambers (634).

Between distal end (614) and proximal end (618), each top (626) and floor (630) defines a plurality of vent openings (628, 632). Each vent opening (628, 632) is generally configured in a longitudinally elongate configuration. However, it should be understood that in other examples, any other suitable configuration can be used. For instance, in some examples, vent openings (628, 632) may take the form of vent openings (616) associated with distal end (614) (e.g., plurality of oval-shaped or circular openings). Of course, any other suitable shape may be used as will be apparent to those of ordinary skill in the art in view of the teachings herein.

Vent openings (628, 632) of the present example are each configured to communicate between the exterior of container (600) and each tray chamber (634) of each tray receiving portion (612). Each vent opening (628, 632) is directly adjacent to central wall (624) such that a single vent opening (628, 632) is configured to communicate with both tray chambers (634) despite the presence of central wall (624).

Sidewalls (622) and central wall (624) of each tray receiving portion (612) together define the lateral extends of each tray chamber (634). In particular, each sidewall (622) is generally at an obtuse angle (instead of vertical) in correspondence with the shape of strip sidewalls (112) of each tissue sample tray (100). Central wall (624) is disposed between each sidewall (112) to thereby define two discrete tray chambers (634) per each tray receiving portion (612). Although sidewalls (622) and central wall (624) are shown in the present example as having certain specific relationships between each other, it should be understood that these relationships are generally dictated by the size and shape of tissue sample strip (110) of tissue sample tray (100). Thus, it should be understood that in other examples, the relationships between sidewalls (622) and central wall (624) can be varied as desired to accommodate trays (100) with differently sized and shaped tissue sample strips (110).

As described above, each tray receiving portion (612) is joined by at least a portion of each distal end (614) being integral with at least a portion of an adjacent distal end (614). In addition, each tray receiving portion (612) in the present example is also connected to an adjacent tray receiving portion (612) by sidewalls (622). Each sidewall (622) that is adjacent to another sidewall (622) of an adjacent tray receiving portion (612) is integrally connected to the adjacent sidewall (622). This integral connection between sidewalls (622) provides additional rigidity to container (600) to support tissue sample tray (100) when at least a portion of tissue sample tray (100) is disposed within each tray receiving portion (612). However, unlike the integral connection sidewalls (222, 322, 422, 522) described above, the integral connection of sidewalls (622) of the present example is configured to provide a living hinge between each tray receiving portion (612). In particular, the integral connection is generally configured to be large enough to secure sidewalls (622) to each other, yet small enough to provide some flexibility. Accordingly, it should be understood that the integral connection between sidewalls (622) is configured to permit flexion of tray receiving portions (612) relative to each other to permit container (600) to transition between the flat configuration and the arcuate configuration.

Although sidewalls (622) are described herein as forming an integral connection that provides a living hinge, it should be understood that in other examples functionality provided by such an integral connection may be provided by any other suitable means. For instance, in some examples sidewalls (622) can be connected to each other by a separate hinged member that can be similar to a door hinge or any other rotatable fastener. Of course, any other structure configured to permit tray receiving portions (612) to flex relative to each other may be used as will be apparent to those of ordinary skill in the art in view of the teachings herein.

Unlike container (200) described above, container (600) of the present example is not shown as including a tab similar to tab (240) described above. However, although not shown, it should be understood that in some examples container (600) can include a tab similar to tab (240) described above. In such examples, such a tab can be configured to permit gripping of container (600) and to permit labeling of container (600). Additionally, such a tab may likewise include a label portion similar to label portion (242) described above. Such a label portion can be recessed such that it is configured to receive a label therein.

Figure 18:
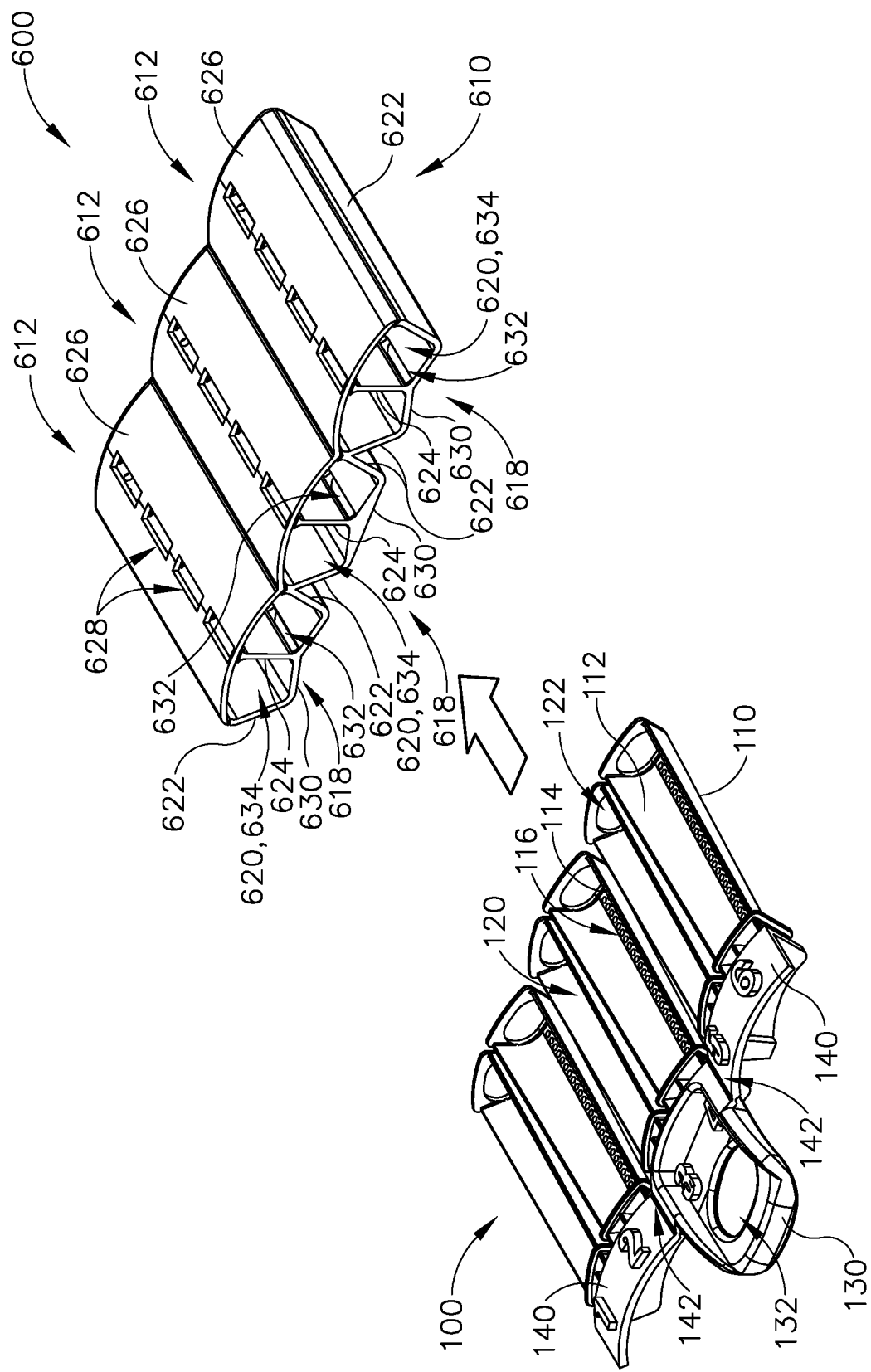
FIG. 18 depicts still another perspective view of the container of FIG. 16, with the tray of FIG. 3 disposed adjacent to the container.

FIGS. 18-21 show an exemplary use of container (600). In particular, as can be seen in FIG. 18, tissue sample tray (100) initially begins outside of container (600). It should be understood that in a biopsy procedure, this initial position of tissue sample tray (100) may correspond to point at which tray has received samples from biopsy device (10) and been removed from rotatable member (44) of tissue sample holder assembly (40). Thus, it should be understood that the procedure described herein may be used to prepare tissue sample tray (100) for post-tissue acquisition specimen radiograph followed by subsequent transport of tissue sample tray (100) to pathology for further analysis.

Once tissue sample tray (100) is positioned adjacent to container (600) as shown in FIG. 18, tissue sample tray (100) may be inserted into container into container (600). To insert tissue sample tray (100) into container (600), each tissue sample strip (110) of tissue sample tray (100) is aligned with a corresponding tray chamber (634) of each tray receiving portion (612). Tissue sample tray (100) is then translated to insert each tissue sample strip (110) into a corresponding tray chamber (634).

Once each tissue sample strip (110) of tissue sample tray (100) is inserted into each tray chamber (634) of each tray receiving portion (612), each tissue sample strip (110) is disposed almost entirely within each tray chamber (634). However, each tissue receiving chamber (120) of each tissue sample strip (110) remains in communication with the exterior of container (600) via vent openings (616, 628, 632). In particular, vent openings (616) associated with distal end (614) are in communication with tissue receiving chamber (120) via distal opening (122). Similarly, vent openings (628) associated with top (626) communicate directly with tissue receiving chamber (120), while vent openings (634) associated with floor (632) communicate with tissue receiving chamber (120) via openings (116) in floor (114).

Figure 19:
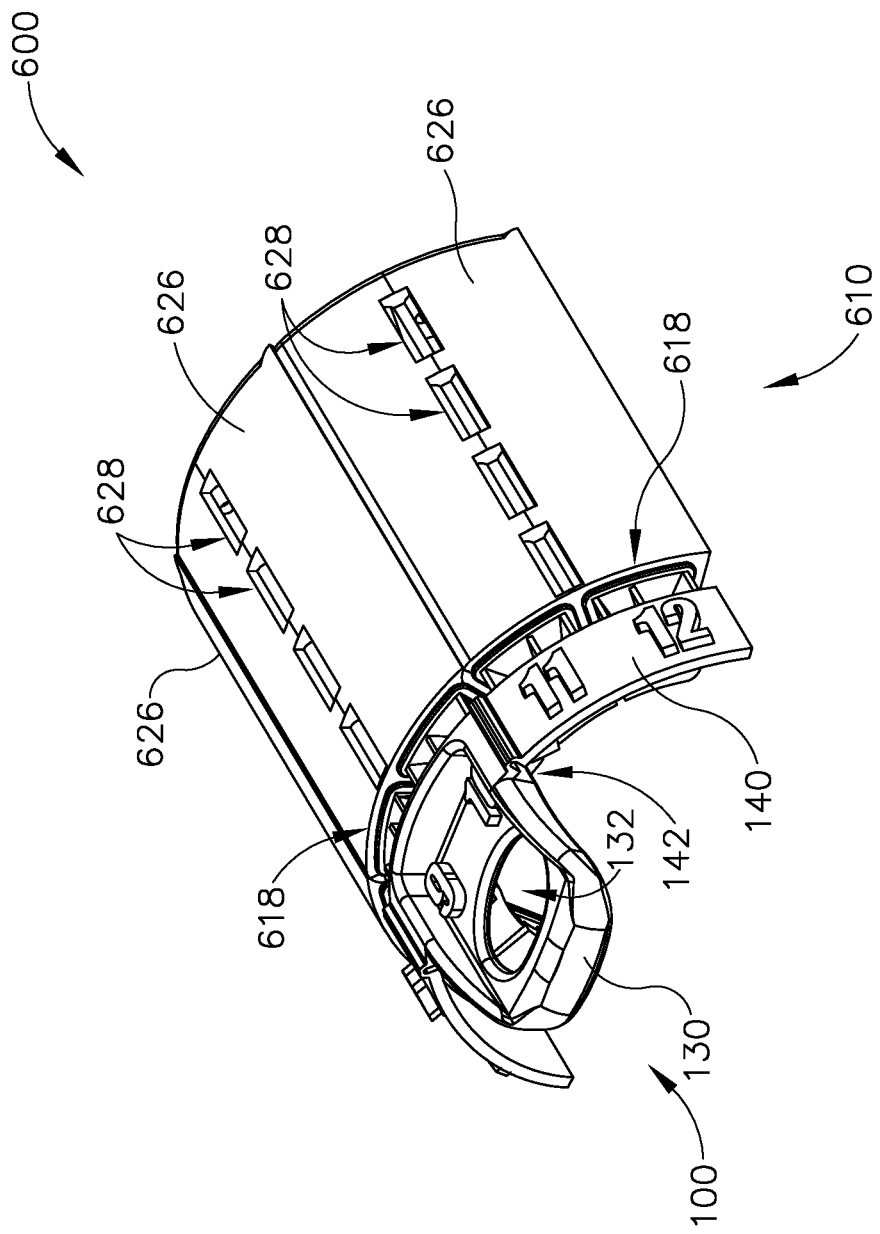
FIG. 19 depicts yet another perspective view of the container of FIG. 16, with at least a portion of the tray of FIG. 3 disposed within the container and the container in an arcuate position.

With each tissue sample strip (110) of tissue sample tray (100) inserted into a corresponding tray chamber (634) of each tray receiving portion (612), container (600) may be next transitioned into the arcuate configuration as shown in FIG. 19. An operator may transition container (600) to the arcuate configuration by generally bending container (600) to pivot each tray receiving portion (612) around the integral connection of each sidewall (622). Alternatively, it should be understood that container (600) may be optionally left in the flat configuration shown in FIG. 18. When left in the flat configuration, container (600) may be handled using a procedure substantially similar to the one described above with respect to container (200).

Before or after transitioning container (600) to the arcuate configuration, an operator may subject container (600) along with tissue sample tray (100) to a specimen radiograph, if such a specimen radiograph is desired. By way of example only, a suitable specimen radiograph procedure may be performed in accordance with at least some of the teachings of U.S. Ser. No. 15/638,740, entitled "Biopsy Sample Container," filed on Jun. 30, 2017, the disclosure of which is incorporated by reference herein.

Figure 20:
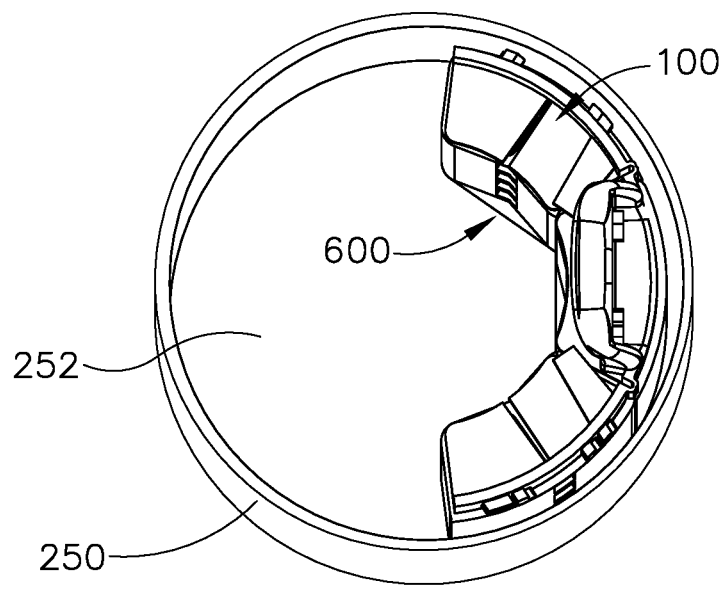
FIG. 20 depicts a top plan view of the container of FIG. 16 and the tray of FIG. 3 disposed within the cup of FIG. 11.

Once specimen radiograph is complete, or if no specimen radiograph is performed, container (300) along with tissue sample tray (100) may be inserted into cup (250) as shown in FIG. 20. As similarly described above with respect to container (200), cup (250) may be used to transport tissue samples such as to a pathology lab. In some instances, cup (250) may be pre-filled with a fixation fluid (252) (e.g., formalin), such that container (600) is immediately immersed in fixation fluid (252). In some other instances, fixation fluid (252) may be introduced to cup (650) after container (200) is first placed in cup (250). In either case, it should be understood that fixation fluid (252) may immediately pass into the interior of container (600) via vent openings (616, 628, 632). Fixation fluid (252) may thereby readily reach and immerse the tissue samples contained within tray chambers (634) in container (600). With container (600) and fixation fluid (252) in cup (250), the operator may then secure cup lid (254) to cup (250), thereby sealing container (600) and fixation fluid (252) in cup (250). After container (600) and fixation fluid (252) are sealed in cup (250), cup (250) may then be transported to another location for further processing, be set aside for storage, or be otherwise handled.

Figure 21:
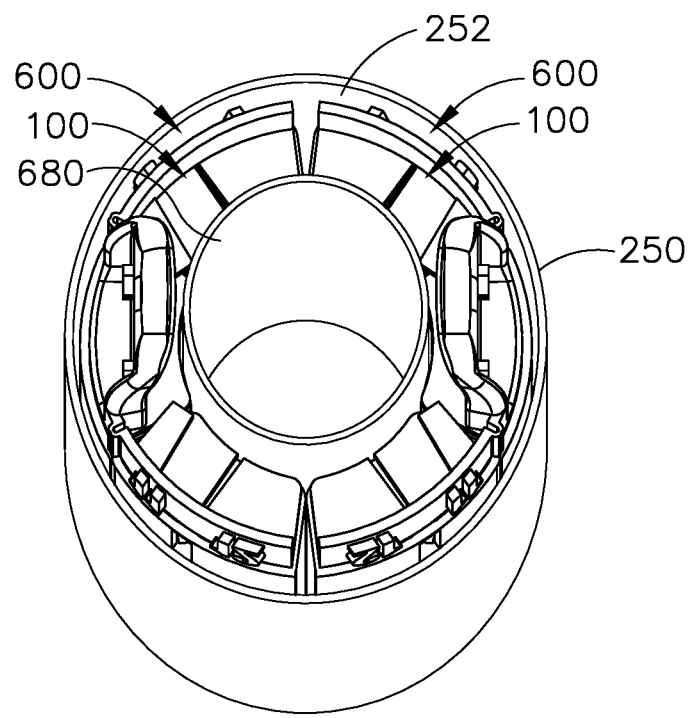
FIG. 21 depicts a perspective view of the container of FIG. 16 and the tray of FIG. 3 disposed within the cup of FIG. 11.

As best seen in FIG. 21, it should be understood that in some examples cup (250) may receive multiple containers (600). In particular, in the present example the lateral width of container (200) approximately corresponds to a predetermined dimension less than inner circumference of cup (250). Because of this, it should be understood that lateral width of container (600) is configured such that up to two containers (600) may be disposed within cup (250) at a time. Optionally, when two containers (600) are disposed in cup (250), a cylindrical member (680) may be inserted within cup (250) within a generally cylindrical space defined by each container (600) in the arcuate configuration. Cylindrical member (680) is configured to generally abut each container (600) to thereby hold each container in position. Of course, cylindrical member (680) is merely optional and may be omitted in some examples.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue acquisition and handling system, comprising: a biopsy device, the biopsy device including a needle and a tissue sample holder assembly, wherein the needle is configured to acquire tissue samples and communicate tissue samples to the tissue sample holder assembly; a tray, wherein the tray includes a plurality of strips, wherein the tray is configured to be received within the tissue sample holder assembly of the biopsy device; and a container, wherein the container includes a plurality of tray receiving portions, wherein each tray receiving portion includes: a distal end, a proximal end, wherein the proximal end includes at least one tray opening, and a tray chamber extending between the proximal end and the distal end, wherein the tray chamber is configured to receive at least a portion of the tray through the tray opening of the proximal end.

Example 2

The system of Example 1, wherein the container further includes a plurality of vent openings, wherein at least one vent opening of the plurality of vent openings is defined by the distal end of each tray receiving portion.

Example 3

The system of Example 2, wherein each tray receiving portion further includes a top and a bottom.

Example 4

The system of Example 3, wherein at least one vent opening of the plurality of vent openings is defined by the top, wherein at least one vent opening of the plurality of vent openings is defined by the bottom.

Example 5

The system of Example 3, wherein each tray receiving portion further includes a pair of sidewalls and a central wall.

Example 6

The system of Example 5, wherein the pair of sidewalls and the central wall of each tray receiving portion defines two tray chambers.

Example 7

The system of Example 6, wherein each tray chamber of the two tray chambers is configured to receive a single strip of the plurality of strips of the tray.

Example 8

The system of any one or more of Examples 1 through 7, wherein the tray opening of the proximal end of each tray receiving portion is configured to slidably receive at least a portion of the tray.

Example 9

The system of any one or more of Examples 1 through 7, wherein each tray receiving portion is configured to receive at least a portion of the tray by dropping the tray into the tray chamber of each tray receiving portion.

Example 10

The system of any one or more of Examples 1 through 9, wherein the container includes three tray receiving portions.

Example 11

The system of Example 10, wherein the tray includes six strips, wherein each tray receiving portion is configured to receive two strips.

Example 12

The system of any one or more of Examples 1 through 11, wherein each tray receiving portion includes a top, wherein the top is pivotable relative to a body of the container.

Example 13

The system of Example 12, wherein the top of each tray receiving portion is interconnected such that each top of each tray receiving portion is configured to pivot relative to the body in unison.

Example 14

The system of Example 12, wherein each top of each tray receiving portion is pivotable laterally relative to the body of the container.

Example 15

The system of Example 12, wherein each top of each tray receiving portion is pivotable longitudinally relative to the body of the container.

Example 16

A container for use with a tissue sample tray, the tissue sample tray comprising a plurality of strips that are configured to receive a tissue sample, the container including: a container body; and a plurality of tray receiving portions, wherein each tray receiving portion includes: a distal end, a proximal end, a top, a floor, and a pair of sidewalls, and a central wall, wherein the distal end, the proximal end, the top, the floor, the pair of sidewalls and the central wall all define a pair of tray chambers, wherein each tray chamber is configured to receive a strip of the plurality of strips of the sample tray, wherein at least one of the distal end, the top, or the floor defines a plurality of vent openings, wherein the plurality of vent openings are configured to communicate fluid between an exterior of the container and at least one tray chamber of the pair of tray chambers.

Example 17

The container of Example 16, wherein the at least one of the top or the floor defines the plurality of vent openings.

Example 18

The container of Example 17, wherein the central wall is disposed relative to each vent opening such that each vent opening is in communication with both tray chambers of the pair of tray chambers.

Example 19

The container of Example 16, wherein the distal end of each tray receiving portion defines at least some of the vent openings of the plurality of vent openings, wherein the vent openings defined by the distal end include a circular shape.

Example 20

A container for use with a tissue sample tray, the tissue sample tray comprising a plurality of strips that are configured to receive a tissue sample, the container including: a container body; a plurality of tray receiving portions, wherein each tray receiving portion includes: a top, a floor, a pair of sidewalls, and a central wall disposed between the pair of sidewalls, wherein the top, the floor, the sidewalls, and the central wall all define a pair of tray chambers, wherein each tray chamber of the pair of tray chambers is configured to receive a strip of the plurality of strips of the tissue sample tray; and a tab extending proximally from the container body, wherein the tab is configured to receive a label.

Example 21

A container for use with a tissue sample tray, the tissue sample tray having a plurality of strips that are configured to receive a tissue sample, the container comprising: a container body; and a plurality of tray receiving portions, wherein each tray receiving portion includes: a distal end, a proximal end, and a plurality of walls; wherein the distal end, the proximal end, plurality of walls all define a pair of tray chambers, wherein each tray chamber is configured to receive a strip of the plurality of strips of the sample tray, wherein at least one of the distal end, or one or more of the plurality of walls defines a plurality of vent openings, wherein the plurality of vent openings are configured to communicate a fixation agent from an exterior of the container and at least one tray chamber of the pair of tray chambers to fix at least one tissue sample, wherein the plurality of walls are configured to surround each strip of the plurality of strips of the sample tray to maintain the at least one tissue sample within a respective tray chamber.

Example 22

The container of Example 21, wherein the plurality of walls includes a top, and a floor, wherein the at least one of the top or the floor defines the plurality of vent openings.

Example 23

The container of Example 22, wherein the plurality of walls further includes a central wall disposed between a pair of sidewalls, wherein the central wall is disposed relative to each vent opening such that each vent opening is in communication with both tray chambers of the pair of tray chambers.

Example 24

The container of Example 21, wherein the distal end of each tray receiving portion defines at least some of the vent openings of the plurality of vent openings, wherein the vent openings defined by the distal end include a circular shape.

Example 25

A method for fixing one or more biopsy samples, the method comprising: collecting one or more tissue samples within a sample tray using a biopsy device; inserting the sample tray into a tray receiver after collecting the one or more tissue samples within the sample tray; and inserting the combination of the sample tray and the tray receiver into a container filled with a fixative agent such that the fixative agent penetrates the tray receiver and surrounds the one or more tissue samples.

Example 26

The method of Example 25, further comprising the step of transporting the container to a pathology laboratory after receiving the combination of the sample tray and tray receiver therein.

Example 27

The method of any one or more of Examples 25 through 26, further comprising the step of transitioning the sample tray from an arcuate configuration to a flat configuration before inserting the sample tray into the tray receiver.

Example 28

The method of any one or more of Examples 25 through 27, further comprising the step of transitioning the combination of the sample tray and the tray receiver to an arcuate configuration prior to inserting the combination of the sample tray and the tray receiver into the container.

Example 29

The method of any one or more of Examples 25 through 28, wherein the step of inserting the sample tray into the tray receiver further includes moving at least a portion of the tray receiver relative to the sample tray to thereby enclose at least a portion of the sample tray.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A container for use with a tissue sample tray, the tissue sample tray having a plurality of strips that are configured to receive a tissue sample, the container comprising:
   (a) a container body; and
   (b) a plurality of tray receiving portions, each tray receiving portion including:
      (i) a distal end,
      (ii) a proximal end, and
      (iii) a plurality of walls;
   the distal end, the proximal end, plurality of walls all defining a pair of tray chambers, each tray chamber being configured to receive a strip of the plurality of strips of the sample tray,
   at least one of the distal end, or one or more of the plurality of walls defining a plurality of vent openings, the plurality of vent openings being configured to communicate a fixation agent from an exterior of the container and at least one tray chamber of the pair of tray chambers to fix at least one tissue sample, the plurality of walls being configured to surround each strip of the plurality of strips of the sample tray to maintain the at least one tissue sample within a respective tray chamber, and
   the plurality of tray receiving portions being defined by the container body along a common plane.

2. The container of claim 1, the plurality of walls including a top, and a floor, the at least one of the top or the floor defining the plurality of vent openings.

3. The container of claim 2, the plurality of walls further including a central wall disposed between a pair of sidewalk, the central wall being disposed relative to each vent opening such that each vent opening is in communication with both tray chambers of the pair of tray chambers.

4. The container of claim 1, the distal end of each tray receiving portion defining at least some of the vent openings of the plurality of vent openings, the vent openings being defined by the distal end including a circular shape.

* * * * *

UNITED STATES PATENT AND TRADEMARK OFFICE
CERTIFICATE OF CORRECTION

| | |
|---|---|
| PATENT NO. | : 10,863,974 B2 |
| APPLICATION NO. | : 15/729262 |
| DATED | : December 15, 2020 |
| INVENTOR(S) | : Bryan R. Keller |

It is certified that error appears in the above-identified patent and that said Letters Patent is hereby corrected as shown below:

In the Claims

Column 30, Claim 3, Line 38, reads "...including a central wall disposed between a pair of sidewalk..."; which should be deleted and replaced with "...including a central wall disposed between a pair of sidewalls...."

Signed and Sealed this
Twelfth Day of July, 2022

Katherine Kelly Vidal
*Director of the United States Patent and Trademark Office*